(12) United States Patent
Ono

(10) Patent No.: US 7,982,094 B2
(45) Date of Patent: Jul. 19, 2011

(54) GENE ENCODING LIGNAN METHYLATION ENZYME

(75) Inventor: Eiichiro Ono, Osaka (JP)

(73) Assignee: Sunitory Holdings Limited, Osaka-shi, Osaka (JP)

( * ) Notice: Subject to any disclaimer, the term of this patent is extended or adjusted under 35 U.S.C. 154(b) by 191 days.

(21) Appl. No.: 11/884,472

(22) PCT Filed: Mar. 27, 2007

(86) PCT No.: PCT/JP2007/057363
§ 371 (c)(1),
(2), (4) Date: Aug. 16, 2007

(87) PCT Pub. No.: WO2007/119639
PCT Pub. Date: Oct. 25, 2007

(65) Prior Publication Data
US 2009/0241226 A1  Sep. 24, 2009

(30) Foreign Application Priority Data
Mar. 29, 2006  (JP) .................................. 2006-090877

(51) Int. Cl.
  C12N 15/82  (2006.01)
  C12N 15/63  (2006.01)
  A01H 5/00   (2006.01)
  C07H 21/04  (2006.01)

(52) U.S. Cl. ........ 800/284; 800/278; 800/295; 800/298; 435/320.1; 435/468; 536/23.1; 536/23.2; 536/23.6

(58) Field of Classification Search .................. None
See application file for complete search history.

(56) References Cited

U.S. PATENT DOCUMENTS
2004/0049802 A1* 3/2004 Dixon et al. ................. 800/278

FOREIGN PATENT DOCUMENTS
WO  WO 2008/069878 A2  6/2008

OTHER PUBLICATIONS

Kato et al., "Biosynthesis of Antioxidant Lignans in *Sesamum Indicum* Seeds," Phytochemistry, vol. 47, No. 4, pp. 583-591, 1998, Pergamon Press, New York, New York.
Gang et al., "Characterization of Phenylpropene O-Methyltransferases from Sweet Basil: Facile Change of Substrate Specificity and Convergent Evolution within a Plant O-Methyltransferase Family," The Plant Cell, vol. 14, pp. 505-519, Feb. 2002, American Society of Plant Physiologists, Kyoto, Japan.
Jones et al., "Isolation and Structure of Sesangolin, a Constituent of *Sesamum angolense* (Welw.)," Journal of Organic Chemistry, 1962, vol. 27, pp. 3232-3235, American Chemical Society, Columbus, Ohio.
Ocimum basilicum caffeic acid O-methyltransferase (COMT2) mRNA, complete cds, GenBank [online], Aug. 25, 1999, Accession No. AF154918 [retrieved on Apr. 20, 2007], retrieved from the United States NCBI web site.
MC01033E10 MC01 Sesamum indicum cDNA, mRNA sequence, GenBank [online], Dec. 31, 2003, Accession No. BU668664 [retrieved on Apr. 30, 2007], retrieved from the United States NCBI web site.
Caffeic acid 3-O-methyltransferase (S-adenosysl-L-methionine: caffeic acid 3-O-methyltransferase) (COMT) (COAMT), GenBank [online], Feb. 7, 2006, Accession No. Q8W013 [retrieved on Apr. 20, 2007], retrieved from the United States NCBI web site.
Toshiaki Umezawa et al., "A Novel O-methyltransferase catalyzing a regioselective methylation of lignan," 49th Lignin Touron Kai Kouen Shu, the 49th Lignin Touron kai Jimukyoku, Oct. 20, 2004, pp. 33-36.
K. Kranz et al., "β-Peltatin 6-O-methyltransferase from suspension cultures of *Linum nodiflorum*," Phytochemistry, 2003, vol. 64, No. 2, pp. 453-458.
Supplementary European Search Report dated Jun. 17, 2009, issued in EP 07740799.
Database Geneseq [Online], "Lignin-modulating polypeptide, SEQ ID 731," XP002532703, Accession No. ARW69314.
International Search Report dated May 1, 2007 in International PCT Application No. PCT/JP2007/057363 filed Mar. 27, 2007.
Database Geneseq [Online], "Lignin-modulating polypeptide, SEQ ID 731," XP002532703, Accession No. ARW69314, 2006.
International Search Report dated May 1, 2007 in International PCT Application No. PCT/JP2007/057363 filed Mar. 27, 2007.

* cited by examiner

*Primary Examiner* — Brent Page
(74) *Attorney, Agent, or Firm* — Drinker Biddle & Reath LLP

(57) ABSTRACT

The present invention relates to genes for enzymes having the activity of transferring a methyl group to lignans, plants with an altered lignan composition using these methyltransferases, and so on. More particularly, the present invention relates to enzyme genes having the activity of synthesizing methylated lignans, preferably enzyme genes having the activity of synthesizing sesame-derived methylated lignans, and use thereof.

13 Claims, 10 Drawing Sheets

2A l:leaves, f:flower, st:stem, sp:seed pod,
Sdl:seedlings, 18S:18s ribosomal RNA

2B l:leaves, f:flower, st:stem, sp:seed pod,
18S:18s ribosomal RNA

6D

US 7,982,094 B2

SEQUENCE LISTING

<160> NUMBER OF SEQ ID NOS: 23

<210> SEQ ID NO 1
<211> LENGTH: 1065
<212> TYPE: DNA
<213> ORGANISM: sesame

<400> SEQUENCE: 1

```
atggcggatc agtccgagga agaagaggct ttcttatacg ccatggagct agcttctgct      60
tctgcgctcc ccatggtact caaatccgcc atagagctgg atctcctcga gctcattaaa     120
aaagctggtc caggagcttc tgtttctccc tcccaactcg cagctcaact tccaaccaaa     180
aaccccgacg cagccaccat gatagatagg atgctccgcc tccttgccgc atactccgtc     240
gtccgctgca gtctgaaacc gcttccagac ggcggcgtgg agcggctcta ctctcttgcg     300
ccggtgtgca gttcctgac caggaatgag gatggggttt ccgtggcccc ggttgcgctc     360
atgcttcagg acaaggtttt catggagtcc tggtatcata taaaagatac agttctggag     420
ggaggaatcc cgttcaacag agcttacggc atgagcgcgt tcgaataccc ggccacggat     480
ccgcgattca acaaggtatt caaccgggca atgtacgaac agtccaccat attcatgaag     540
caaatacttg aaaaatacaa agggtttgag ggggtgaaat cgctggtgga tgtgggtggt     600
ggcatcggag cttcgcttaa atgatcctca tccaagtacc ccaccattaa gggcatcaac     660
tttgacttgc cccatgtcat tcaagatgct ccatcttttc cgggagtgga gcatgtcggc     720
ggcgacatgt ttgtgagtgt gcccaaagcc gacgcgattt ttatgaagtg gatttgccac     780
gactggagcg acgcgcactg ccagaagctg ttgaagaact gctatgacgc acttccggat     840
aatgaaaaag tgatcatcgc ggacagcatt ttcccgttag acccaacag tgggccggct     900
ttcaagcggg tggcccacgg cgatgtcatc atgttagcct taaacccggg tgggaaggag     960
aggtcagaaa aggaatttca gagcttggcc caatacgcgg gcttcagaga agtcataaaa    1020
gtgtactctg ctttcaatat ttggatcatg gaatttcata agtga                    1065
```

<210> SEQ ID NO 2
<211> LENGTH: 354
<212> TYPE: PRT
<213> ORGANISM: seame

<400> SEQUENCE: 2

```
Met Ala Asp Gln Ser Glu Glu Glu Ala Phe Leu Tyr Ala Met Glu
1               5                   10                  15

Leu Ala Ser Ala Ser Ala Leu Pro Met Val Leu Lys Ser Ala Ile Glu
            20                  25                  30

Leu Asp Leu Leu Glu Leu Ile Lys Lys Ala Gly Pro Gly Ala Ser Val
        35                  40                  45

Ser Pro Ser Gln Leu Ala Ala Gln Leu Pro Thr Lys Asn Pro Asp Ala
    50                  55                  60

Ala Thr Met Ile Asp Arg Met Leu Arg Leu Leu Ala Ala Tyr Ser Val
65                  70                  75                  80

Val Arg Cys Ser Leu Lys Pro Leu Pro Asp Gly Gly Val Glu Arg Leu
                85                  90                  95

Tyr Ser Leu Ala Pro Val Cys Lys Phe Leu Thr Arg Asn Glu Asp Gly
            100                 105                 110

Val Ser Val Ala Pro Val Ala Leu Met Leu Gln Asp Lys Val Phe Met
        115                 120                 125
```

```
Glu Ser Trp Tyr His Ile Lys Asp Thr Val Leu Glu Gly Gly Ile Pro
        130                 135                 140

Phe Asn Arg Ala Tyr Gly Met Ser Ala Phe Glu Tyr Pro Ala Thr Asp
145                 150                 155                 160

Pro Arg Phe Asn Lys Val Phe Asn Arg Ala Met Tyr Glu Gln Ser Thr
                165                 170                 175

Ile Phe Met Lys Gln Ile Leu Glu Lys Tyr Lys Gly Phe Glu Gly Val
            180                 185                 190

Lys Ser Leu Val Asp Val Gly Gly Ile Gly Ala Ser Leu Lys Met
        195                 200                 205

Ile Leu Ser Lys Tyr Pro Thr Ile Lys Gly Ile Asn Phe Asp Leu Pro
        210                 215                 220

His Val Ile Gln Asp Ala Pro Ser Phe Pro Gly Val Glu His Val Gly
225                 230                 235                 240

Gly Asp Met Phe Val Ser Val Pro Lys Ala Asp Ala Ile Phe Met Lys
                245                 250                 255

Trp Ile Cys His Asp Trp Ser Asp Ala His Cys Gln Lys Leu Leu Lys
            260                 265                 270

Asn Cys Tyr Asp Ala Leu Pro Asn Gly Lys Val Ile Ile Ala Asp
        275                 280                 285

Ser Ile Phe Pro Leu Gly Pro Asn Ser Gly Pro Ala Phe Lys Arg Val
        290                 295                 300

Ala His Gly Asp Val Ile Met Leu Ala Leu Asn Pro Gly Gly Lys Glu
305                 310                 315                 320

Arg Ser Glu Lys Glu Phe Gln Ser Leu Ala Gln Tyr Ala Gly Phe Arg
                325                 330                 335

Glu Val Ile Lys Val Tyr Ser Ala Phe Asn Ile Trp Ile Met Glu Phe
            340                 345                 350

His Lys

<210> SEQ ID NO 3
<211> LENGTH: 1065
<212> TYPE: DNA
<213> ORGANISM: sesame

<400> SEQUENCE: 3
atggcggagc agtccgagga agaagaggct ttcttattcg caatggagat agctaccgct      60
tctgtgctcc ccatggtact caaatccgcc atagagctgg atctcctcga gctgattaaa     120
aaagctggtc caggagcttc tgcttctccc tccaactcg cagctcaact tcaacctcaa     180
aaccccgacg cagccaccat gattgatagg atgctccgct cctcgcggc acactccgtc     240
ctccgctgca ccctgaaacc gcttccagac ggcggcgtgg agcggcgcta ctccctggcg     300
ccggtgtgca agttcctgac caggaatgag gatggggttt ctctggcccc tgttgcgctc     360
atgcttcagg acaaggtttt gatggagtcc tggtatcatc tgaaagacac agttctggag     420
ggaggaattc cgttcaacag agcgcacggc atgagtgcgt tcgagtaccc ggccgtggat     480
ccgcgattca acaaggtatt caaccagggt atgtacgaac agtccaccat tttcatgaag     540
caaatacttg aaaaatacaa agggtttgag ggggtgaagt cgctggtgga tgtgggtggt     600
ggcatcggag cttcgcttaa gatgatccta tccaaatacc cgtccattaa ggccatcaac     660
ttcgacttgc cccatgtcat tcaagatgct ccatcttatc cgggagtgga gcatattggc     720
ggcgacatgt ttgttagtgt gcccaaagcc gacgcgattt ttatgaagtg gatttgccac     780
gactggagcg acgcgcaccg ccagaagctg ttgaagaact gctacgaagc acttccgaat     840
```

```
aatggaaaag tgatcatcgc tgatagcatt ctcccggagg atccaaatag tgggtcggct      900
ttcaggcgcg cggcccaggg cgatgtcatc atgttagcct ttaatccagg tgggaaggag      960
agatcagaaa aggaatttca ggccttggcc cagtacgccg gcttcagaga agttataaaa     1020
gtatgctccg ctttcaatat ttggatcatg gaatttcata agtga                    1065
```

<210> SEQ ID NO 4
<211> LENGTH: 354
<212> TYPE: PRT
<213> ORGANISM: sesame

<400> SEQUENCE: 4

```
Met Ala Glu Gln Ser Glu Glu Glu Ala Phe Leu Phe Ala Met Glu
1               5                   10                  15

Ile Ala Thr Ala Ser Val Leu Pro Met Val Leu Lys Ser Ala Ile Glu
            20                  25                  30

Leu Asp Leu Leu Glu Leu Ile Lys Lys Ala Gly Pro Gly Ala Ser Ala
        35                  40                  45

Ser Pro Ser Gln Leu Ala Ala Gln Leu Gln Pro Gln Asn Pro Asp Ala
    50                  55                  60

Ala Thr Met Ile Asp Arg Met Leu Arg Phe Leu Ala Ala His Ser Val
65                  70                  75                  80

Leu Arg Cys Thr Leu Lys Pro Leu Pro Asp Gly Gly Val Glu Arg Arg
                85                  90                  95

Tyr Ser Leu Ala Pro Val Cys Lys Phe Leu Thr Arg Asn Glu Asp Gly
            100                 105                 110

Val Ser Leu Ala Pro Val Ala Leu Met Leu Gln Asp Lys Val Leu Met
        115                 120                 125

Glu Ser Trp Tyr His Leu Lys Asp Thr Val Leu Glu Gly Gly Ile Pro
    130                 135                 140

Phe Asn Arg Ala His Gly Met Ser Ala Phe Glu Tyr Pro Ala Val Asp
145                 150                 155                 160

Pro Arg Phe Asn Lys Val Phe Asn Gln Gly Met Tyr Glu Gln Ser Thr
                165                 170                 175

Ile Phe Met Lys Gln Ile Leu Glu Lys Tyr Lys Gly Phe Glu Gly Val
            180                 185                 190

Lys Ser Leu Val Asp Val Gly Gly Gly Ile Gly Ala Ser Leu Lys Met
        195                 200                 205

Ile Leu Ser Lys Tyr Pro Ser Ile Lys Ala Ile Asn Phe Asp Leu Pro
    210                 215                 220

His Val Ile Gln Asp Ala Pro Ser Tyr Pro Gly Val Glu His Ile Gly
225                 230                 235                 240

Gly Asp Met Phe Val Ser Val Pro Lys Ala Asp Ala Ile Phe Met Lys
                245                 250                 255

Trp Ile Cys His Asp Trp Ser Asp Ala His Arg Gln Lys Leu Leu Lys
            260                 265                 270

Asn Cys Tyr Glu Ala Leu Pro Asn Asn Gly Lys Val Ile Ile Ala Asp
        275                 280                 285

Ser Ile Leu Pro Glu Asp Pro Asn Ser Gly Ser Ala Phe Arg Arg Ala
    290                 295                 300

Ala Gln Gly Asp Val Ile Met Leu Ala Phe Asn Pro Gly Gly Lys Glu
305                 310                 315                 320

Arg Ser Glu Lys Glu Phe Gln Ala Leu Ala Gln Tyr Ala Gly Phe Arg
                325                 330                 335

Glu Val Ile Lys Val Cys Ser Ala Phe Asn Ile Trp Ile Met Glu Phe
```

His Lys

<210> SEQ ID NO 5
<211> LENGTH: 17
<212> TYPE: DNA
<213> ORGANISM: artificial
<220> FEATURE:
<223> OTHER INFORMATION: primer

<400> SEQUENCE: 5
caggaaacag cattgac                                          17

<210> SEQ ID NO 6
<211> LENGTH: 17
<212> TYPE: DNA
<213> ORGANISM: artificial
<220> FEATURE:
<223> OTHER INFORMATION: primer

<400> SEQUENCE: 6
gtaaaacgac ggccagt                                          17

<210> SEQ ID NO 7
<211> LENGTH: 21
<212> TYPE: DNA
<213> ORGANISM: artificial
<220> FEATURE:
<223> OTHER INFORMATION: primer

<400> SEQUENCE: 7
ttgccccatg tcattcaaga t                                     21

<210> SEQ ID NO 8
<211> LENGTH: 27
<212> TYPE: DNA
<213> ORGANISM: artificial
<220> FEATURE:
<223> OTHER INFORMATION: primer

<400> SEQUENCE: 8
aaaattcaga cttataacga taccaaa                               27

<210> SEQ ID NO 9
<211> LENGTH: 24
<212> TYPE: DNA
<213> ORGANISM: artificial
<220> FEATURE:
<223> OTHER INFORMATION: primer

<400> SEQUENCE: 9
ttagaaaaac tcaattcgtc taat                                  24

<210> SEQ ID NO 10
<211> LENGTH: 24
<212> TYPE: DNA
<213> ORGANISM: artificial
<220> FEATURE:
<223> OTHER INFORMATION: primer

<400> SEQUENCE: 10
cctacatcca cgacggaatc caaa                                  24

<210> SEQ ID NO 11
<211> LENGTH: 21
<212> TYPE: DNA

<213> ORGANISM: artificial
<220> FEATURE:
<223> OTHER INFORMATION: primer

<400> SEQUENCE: 11
tatgcttgtc tcaaagatta a                                    21

<210> SEQ ID NO 12
<211> LENGTH: 21
<212> TYPE: DNA
<213> ORGANISM: artificial
<220> FEATURE:
<223> OTHER INFORMATION: primer

<400> SEQUENCE: 12
aacatctaag ggcatcacag a                                    21

<210> SEQ ID NO 13
<211> LENGTH: 30
<212> TYPE: DNA
<213> ORGANISM: artificial
<220> FEATURE:
<223> OTHER INFORMATION: primer

<400> SEQUENCE: 13
ccggcccact gttcgggtcc taacgggaaa                           30

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
gcaaatccac ttcataaaaa t                                    21

<210> SEQ ID NO 15
<211> LENGTH: 30
<212> TYPE: DNA
<213> ORGANISM: artificial
<220> FEATURE:
<223> OTHER INFORMATION: primer

<400> SEQUENCE: 15
cctcgggttc cgctctttct gctcccagaa                           30

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
atcaatttgg gaaattacaa a                                    21

<210> SEQ ID NO 17
<211> LENGTH: 30
<212> TYPE: DNA
<213> ORGANISM: artificial
<220> FEATURE:
<223> OTHER INFORMATION: primer

<400> SEQUENCE: 17
gaagatcgcc ccatgagcat gaaacccttt                           30

```
<210> SEQ ID NO 18
<211> LENGTH: 24
<212> TYPE: DNA
<213> ORGANISM: artificial
<220> FEATURE:
<223> OTHER INFORMATION: primer

<400> SEQUENCE: 18
aacgtcgttc tgggagcaga aaga                                          24

<210> SEQ ID NO 19
<211> LENGTH: 1068
<212> TYPE: DNA
<213> ORGANISM: sesame

<400> SEQUENCE: 19
atggcgatgg ttaaccaaaa gcaaaatctt gaggtacttg aagctgaagc tcacatttgg    60
aatcaggtgt tcaactacat aaactccatg tcactgaaat gtgcaactga gcttggcatc   120
cctgacgtca tccacaagca tggcggcccg atgaccctga ctgaactgct agatgctctc   180
ccggctgtcg acaaagccaa agccaattgc atgtaccgtc tcatgcgaac cctcgtgcac   240
tctggcttct ttgtattaga aaaactcaat tcgtctaatg aggagggcta ttcgcttacg   300
cctgctccac gtcttttggt cggagatcgc cccatgagca tgaaacccct tgtaatttcc   360
caaattgatc ccatccttac tgagtcgatg caccatttgg gtagatggtt ccaaactact   420
catgaccgca cgacgtttca tattgccaat aacggaacgt cgttctggga gcagaaagag   480
cggaacccga ggtttagcca tttgtttgat caaggcatgg aaagtgatac tccaatggtg   540
gccagcgtca ttactagaga ttgtaggcaa gtgtttgagg gtttggattc cgtcgtggat   600
gtaggcggag gcactggaac tttggccaag gccatagccg aggcgttccc tcaaattcat   660
tgtacagtgc ttgatctacc acatattgtt gcgggattgg aggggagaag gaacttgaag   720
tatattgagg gaaatatgtt cgactatatt ccccatcag atgcagttgt gctcaagtgg    780
ttacttcatg attggagcga tgaggaaagt gtcaagatac tgaagaaatg taaagaagca   840
gtaacgagca atggaaagag agggaaggtg ataatcatcg atatggtggt gaaggagaat   900
gaatcagttg aaactcaact cctccttgac atgctcatga tggctttagt tggaggaaaa   960
gaaagaacgg aaaaagaatg ggcagatctc atttctgacg ctggctttag tggttatagg  1020
atttatcctg ttttgccatt gagatctatc atcgagatat atccttaa               1068

<210> SEQ ID NO 20
<211> LENGTH: 41
<212> TYPE: DNA
<213> ORGANISM: artificial
<220> FEATURE:
<223> OTHER INFORMATION: primer

<400> SEQUENCE: 20
aaaacatgta tggcggatca gtccgaggaa gaagaggctt t                       41

<210> SEQ ID NO 21
<211> LENGTH: 35
<212> TYPE: DNA
<213> ORGANISM: artificial
<220> FEATURE:
<223> OTHER INFORMATION: primer

<400> SEQUENCE: 21
attgtcgact tatgaaattc catgatccaa atatt                              35
```

```
<210> SEQ ID NO 22
<211> LENGTH: 39
<212> TYPE: DNA
<213> ORGANISM: artificial
<220> FEATURE:
<223> OTHER INFORMATION: primer

<400> SEQUENCE: 22
aaaggatcca tggcgatggt taaccaaaag caaaatctt                              39

<210> SEQ ID NO 23
<211> LENGTH: 39
<212> TYPE: DNA
<213> ORGANISM: artificial
<220> FEATURE:
<223> OTHER INFORMATION: primer

<400> SEQUENCE: 23
aaactcgagt taaggatata tctcgatgat agatctcaa                              39
```

GENE ENCODING LIGNAN METHYLATION ENZYME

CROSS REFERENCE TO RELATED APPLICATIONS

This application is the National Stage of International Application No. PCT/JP2007/057363, filed Mar. 27, 2007, and claims benefit of Japanese Application No. 090877/2006, filed Mar. 29, 2006, both of which are herein incorporated by reference in their entirety.

REFERENCE TO A SEQUENCE LISTING

A Sequence Listing containing SEQ ID NOS: 1-23 is incorporated herein by reference.

TECHNICAL FIELD

The present invention relates to genes for enzymes having an activity of transferring a methyl group to lignans, plants with altered lignan compositions using these methyltransferases, and so on. More particularly, the present invention relates to enzyme genes having the activity of synthesizing methylated lignans, preferably enzyme genes having the activity of synthesizing sesame-derived methylated lignans, and use thereof.

BACKGROUND ART

Sesame (*Sesamum indicum*) is an annual plant in the family Pedaliaceae belonging to the genus *Sesamum*. Sesame is said to be indigenous to Central Africa. Sesame is supposedly the oldest domesticated oil seed crop having about a 6000 year history and has been cultivated throughout the world. Sesame is a valuable food from ancient times and known to represent healthy foods. Sesame seeds, oil pressed from sesame seeds and extracts from sesame seeds are particularly utilized (see, e.g., Goma: SONO-KAGAKU-TO-KINOSEI (Sesame: Science and Function), edited by Mitsuo Namiki, Maruzen Planet Publishing Co. (1998)). The components contained in sesame seeds are about 50% lipids and about 20% proteins. The major components of lipids contained in sesame are triglycerides mainly composed of oleic acid and linoleic acid. Furthermore, sesame contains vitamins $B_1$, $B_2$, E, etc. In addition to the components described above, secondary metabolites (e.g., sesamin, sesamolin, etc.) of plants collectively referred to as lignans are contained in sesame, and these components have potent anti-oxidative properties (see, e.g., Biochemical Systematics and Ecology, 13, 133-139 (1985)).

As to biosynthesis of lignans, reference is made to, e.g., Lignans: Biosynthesis and Function, Comprehensive Natural Products Chemistry, 1: 640-713 (1999); Phytochemistry Rev., 2257-288 (2003), etc.

For example, Phytochemistry Rev., 2257-288 (2003) discloses that pinoresinol synthesized through polymerization of coniferyl alcohol is the first lignan in the biosynthetic pathway and from pinoresinol a wide variety of lignans are synthesized via biosynthetic pathways inherent to individual plant species. It is reported that dirigent proteins involved in synthesis of this pinoresinol are localized in Forsythia intermedia, etc. (see, e.g., Science, 275, 362-366 (1997), etc.). In addition, pinoresinol-lariciresinol reductases genes from Forsythia intermedia (see, e.g., J. Biol. Chem., 271: 29473 (1996), Japanese National Publication (Tokuhyo) No. 2001-507931, etc.), pinoresinol-lariciresinol genes from *Thuja plicata* (see, e.g., J. Biol. Chem., 274: 618 (1999), etc.) as well as recombinant secoisolariciresinol dehydrogenase and its use (see, e.g., J. Biol. Chem., 276 (16): 12614-23 (2001), Japanese National Publication (Tokuhyo) No. 2002-512790, etc.) are reported. Besides the larreatricin hydroxylase gene are cloned from Larrea tridentate (see, e.g., Proc. Nat. Acad. Sci. USA, 100: 10641 (2003), etc.).

In the sesame lignan biosynthesis, it was speculated that piperitol synthase would act on pinoresinol to synthesize piperitol and in turn sesamin synthase would act on this piperitol to synthesize sesamin. However, it has become clear that cytochrome P450 cloned from *S. indicum*, i.e., CYP81Q1, that alone gives sesamin from pinoresinol via piperitol (WO 2005/030944; cf. FIG. 1).

In recent years, attention has been drawn not only to lignans but to methylated lignans. It is known that some of the lignan molecules described above are present in plants as glycosides. For instance, sesaminol glycosides (sesaminol 2'-O-β-D-glucopyranoside; sesaminol 2'-O-β-D-glucopyranosyl (1-2)-O-β-D-glucopyranoside; and sesaminol 2'-O-β-D-glucopyranosyl (1-2)-O-(-β-D-glucopyranosyl(1-6))-β-D-glucopyranoside)), and pinoresinol glycosides (pinoresinol 4'-O-β-D-glucopyranosyl (1-6)-β-D-glucopyranoside; pinoresinol 4'-O-β-D-glucopyranosyl (1-2)-β-D-glucopyranoside; pinoresinol 4'-O-β-D-glucopyranosyl (1-6)-O-(β-D-glucopyranosyl (1-6)) β-D-glucopyranoside; and pinoresinol di-O-β-D-glucopyranoside)), etc. are present in sesame seeds; (+)-pinoresinol 4'-O-β-D-glucoside and (−)-matairesinol-4-O-glucoside, etc. are present in Forsythia intermedia; and secolariciresinol diglucoside and pinoresinol diglucoside, etc. are present in *Linum usitatissimum* (see, e.g., Journal of Natural Medicines, 32, 194 (1978), Tetrahedron, 14: 649 (2003) and Phytochemistry, 58: 587 (2001)).

Pinoresinol glycosides and sesaminol glycosides contained in sesame (see, e.g., Katsuzaki, H. et al., Biosci. Biotech. Biochem., 56, 2087-2088 (1992)) show potent antioxidative properties in the water-soluble region, and are expected to yield different applications than lipophilic antioxidants (e.g., tocopherol). Also, the following mechanism of action is proposed for lignan glycosides. In lignan glycosides, the phenolic hydroxyl group, which is a functional group exhibiting antioxidative effect, is protected by sugars which themselves have but taken up into the body and then hydrolyzed by the action of β-glucosidase from enterobacteria to produce lipophilic lignans as the aglycone portion. This aglycone is absorbed into the intestines and carried to various organs via the blood to prevent oxidative damages in biomembranes of the organs, etc. Based on the action mechanism, lignan glycosides are expected to involve applications as preventive diets for arteriosclerosis (see, e.g., T. Osawa: Anticarcinogenesis and Radiation Protection 2: p. 327, Plenum Press, New York (1991)).

Methylated lignans are known as lignan derivatives other than lignan glycosides. Like lignan glycosides, methylated lignans are also lignans, which phenolic hydroxyl groups that are the functional groups relevant for antioxidative properties are blocked by methyl groups and the methoxy structure is thus assigned. It is reported that the furofuran type lignans include kobusin which is methylated piperitol in its 4-hydroxy group and sesangolin which is methylated sesaminol in its 2' hydroxy group (cf. Phytochemistry, 47, 583-591 (1998); and J. Org. Chem., 27, 3232-3235 (1962)) (FIG. 1). However, enzymes that catalyze these synthetic reactions are unknown and so far no report has been made on purification or isolation of the enzymes for methylation of furofuran type lignans and genes encoding the same.

It is known that proteins having the particular function to catalyze transmethylation have similar amino acid sequences even in plants of different species (see, e.g., Plant Cell, 14, 505-519 (2002)).

DISCLOSURE OF THE INVENTION

The biosynthetic pathways of secondary metabolites in plants are altered to produce useful substances and/or breed useful plants. Such a technology is called metabolic engineering. Use of such a technology enables to produce optional compounds in a large scale and/or prevent the production of unwanted substances. Accordingly, it is industrially useful to synthesize lignans and their metabolites by metabolic engineering using the genes involved in the lignan metabolic pathway, in view of the utility of these substances as described above. However, findings on the genes involved in the biosynthesis of lignans, especially furofuran type lignans as typified by sesame lignans are so limited as described above. Besides, any methyltransferase which catalyzes the production of methylated furofuran type lignans is not found. It has thus been desired to acquire additional genes.

In view of the foregoing circumstances, the present invention has been made and provides enzymes having the lignan transmethylation activity, polynucleotides encoding the enzymes, vectors/cells/transformants, etc. comprising the polynucleotides, and so on, which are described below.

(1) A polynucleotide as defined in any one of (a) through (d) below:

(a) a polynucleotide comprising a polynucleotide consisting of the nucleotide sequence of SEQ ID NO:1 or 3;

(b) a polynucleotide comprising a polynucleotide encoding a protein consisting of the amino acid sequence of SEQ ID NO: 2 or 4;

(c) a polynucleotide, which hybridizes to a polynucleotide consisting of a part or the whole of a nucleotide sequence complementary to the nucleotide sequence of SEQ ID NO: 1 or 3 under high stringent conditions and encodes a protein having an activity of transferring a methyl group to a lignan; and, (d) a polynucleotide comprising a polynucleotide encoding a protein consisting of the amino acid sequence of SEQ ID NO: 2 or 4 wherein one or more amino acids are deleted, substituted, inserted and/or added and having an activity of transferring a methyl group to a lignan.

(2) The polynucleotide according to (1) above, which has the amino acid sequence of SEQ ID NO: 2 or 4 or a modified amino acid sequence wherein one or several amino acids are added, deleted and/or substituted with other amino acids in said amino acid sequence and encodes a protein having an activity of transferring a methyl group to a lignan.

(3) The polynucleotide according to (1) above, which hybridizes to a polynucleotide consisting of a nucleotide sequence complementary to a part or the whole of a nucleotide sequence of SEQ ID NO: 1 or 3 under stringent conditions and encodes a protein having an activity of transferring a methyl group to a lignan.

(4) The polynucleotide according to (1) above, which hybridizes to a polynucleotide consisting of a nucleotide sequence complementary to a part or the whole of a nucleotide sequence of SEQ ID NO: 1 or 3 under conditions of 5×SSC at 50° C. and encodes a protein having an activity of transferring a methyl group to a lignan.

(5) The polynucleotide according to (1) above, which comprises a polynucleotide consisting of the nucleotide sequence of SEQ ID NO: 1 or 3.

(6) The polynucleotide according to (1) above, which comprises a polynucleotide encoding a protein consisting of the amino acid sequence of SEQ ID NO: 2 or 4.

(7) The polynucleotide according to any one of (1) through (6) above, which is a DNA.

(8) The polynucleotide according to any one of (1) through (7) above, which encodes a protein having an activity of transferring a methyl group to a furofuran lignan.

(9) The polynucleotide according to (8) above, which encodes a protein having an activity of transferring a methyl group to pinoresinol and/or piperitol.

(10) A protein encoded by the polynucleotide according to any one of (1) through (9) above.

(11) A vector comprising the polynucleotide according to any one of (1) through (9) above.

(12) A host cell transformed by the vector according to (11) above.

(13) A method of producing a protein having an activity of transferring a methyl group to a lignan, which comprises culturing or growing the host cell according to (12) above and collecting said protein from said host cell.

(14) A plant transformed with the polynucleotide according to any one of (1) through (9) above, or a plant which is a progeny of said plant having the same properties as the plant, or a tissue of these plants.

(15) A method of transferring a methyl group to a lignan, which comprises using the polynucleotide according to any one of (1) through (9) above.

(16) A plant with an altered lignan composition produced by transformation and expression of said plant with the polynucleotide according to any one of (1) through (9) above, or a plant which is a progeny of the plant having the same properties as the plant.

(17) A polynucleotide comprising a fragment or complementary sequence of the polynucleotide according to (1) through (9) above.

Use of the polypeptide (lignan methyltransferase) of the present invention provides the effect that the contents of lignans and methylated lignans in organisms (especially in plants) can be artificially regulated. In addition, lignans can be methylated using these recombinant enzymes to alter physical properties (solubility, absorption efficiency in animal, etc.) in vitro and in vivo. Furthermore by using the polynucleotide of the present invention, the methylated lignans not identified so far in nature can be produced artificially. The methylated lignans synthesized using the polypeptide of the present invention can also be used as starting materials or intermediates to develop substances having novel physiological functions.

By expressing the lignan methyltransferase of the present invention in a desired organism using genetic recombination technology, monomethylated pinoresinol can be artificially produced from pinoresinol and/or kobusin from piperitol. Also, the lignan methyltransferase of the present invention can be expressed in a desired organism using genetic recombination technology thereby to prepare plants and/or microorganisms with artificially controlled amounts of lignans and methylated lignans.

Further by repressing the expression of the lignan methyltransferase of the present invention in kobusin- or monomethylated pinoresinol-producing plants, the aglycones can be released to increase the amounts of lignans (especially piperitol and/or pinoresinol).

Furthermore, by using the lignan methyltransferase of the present invention, monomethylated pinoresinol which is a novel methylated lignan can be artificially produced from pinoresinol.

BRIEF DESCRIPTION OF THE DRAWINGS

FIG. 2-2A is the results of gene expression analysis of SiOMT1 and SiOMT2 (*S. indicum* cv. Masekin) in each part of sesame by RT-PCR. FIG. 2-2B is the results of gene expression analysis of SrOMT1 (*S. radiatum*) in each part of sesame by RT-PCR.

FIG. 3-3A is the A280 nm chromatogram in the enzyme reaction solution of SiOMT1 expressed in *Escherichia coli* with pinoresinol. FIG. 3-3B is the A280 nm chromatogram in the enzyme reaction solution of SiOMT1 expressed in *Escherichia coli* with piperitol.

FIG. 4-3C is the A280 nm chromatogram in the enzyme reaction solution of SiOMT2 expressed in *Escherichia coli* with pinoresinol. FIG. 4-3D is the A280 nm chromatogram in the enzyme reaction solution of SiOMT2 expressed in *Escherichia coli* with piperitol.

FIG. 5-3E is the A280 nm chromatogram in the enzyme reaction solution of SrOMT1 expressed in *Escherichia coli* with pinoresinol. FIG. 5-3F is the A280 nm chromatogram in the enzyme reaction solution of SrOMT1 expressed in *Escherichia coli* with piperitol.

FIG. 6-4A is the LC-MS chromatogram of methylated pinoresinol produced by SiOMT1.

FIG. 7-4B is the LC-MS chromatogram of methylated piperitol (kobusin) produced by SiOMT1.

FIG. 9-6A is the A280 nm chromatogram of caffeic acid as a reference standard. FIG. 9-6B is the A280 nm chromatogram in the enzyme reaction solution of SiOMT1 expressed in *Escherichia coli* with caffeic acid. FIG. 9-6C is the A280 nm chromatogram in the enzyme reaction solution of SrOMT1 expressed in *Escherichia coli* with pinoresinol.

FIG. 10-6D is the LC-MS chromatogram of methylated caffeic acid (ferulic acid) produced by SiOMT1.

BEST MODE FOR CARRYING OUT THE INVENTION

Figure 1:
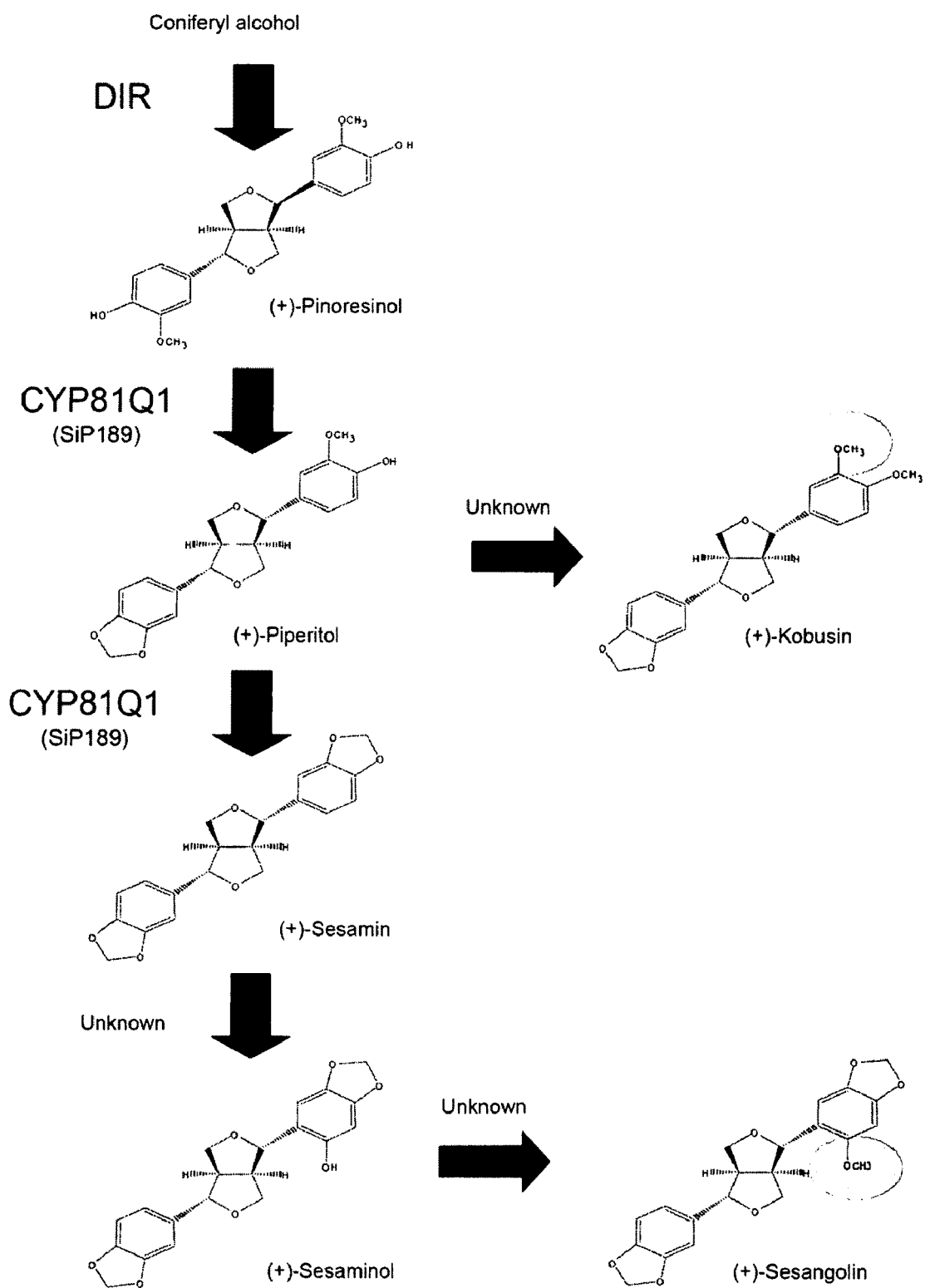
FIG. 1 is the structure and metabolic pathway of sesame lignan.

The present inventors have found novel methyltransferases, whose main substrates are lignans, especially pinoresinol and/or piperitol, and have further found that these methyltransferases catalyze methylation of pinoresinol. Eudesmin, which is dimethylated pinoresinol, has been identified so far but monomethylated pinoresinol has not been found yet.

The inventors searched a partial sequence for sesame methyltransferase-like genes from the EST database of 5000 clones derived from sesame seeds by homology search and as a result, obtained two methyltransferase-like genes (hereinafter SiOMT1 and SiOMT2). These SiOMT genes were strongly expressed in seeds. These full-length nucleotide sequences were obtained by the RACE method and expressed in *Escherichia coli*. After the resulting recombinant protein was reacted with sesaminol or pinoresinol, the enzyme activity was assayed by the HPLC, LC-MS and TOF-MS/MS analyses. The results revealed that SiOMT1 had the activity to catalyze the reaction of methylating piperitol to produce kobusin. The results further revealed that SiOMT1 had the activity to catalyze the reaction of methylating pinoresinol to produce monomethylated pinoresinol. The methylated lignan is considered to be an intermediate for eudesmin, which is a pinoresinol derivative. The SrOMT1 gene, which is a SiOMT1 homolog, was cloned from African sesame *Sesamum radiatum* by PCR, confirming that SrOMT1 has a methylation activity similar to SiOMT1.

"Lignans" are compounds in which two phenylpropanoid molecules having the $C_6C_3$ skeleton are dimerized mostly through the 8-8' position (8,8'-linkage). Lignans are considered to contribute to biological defense mechanisms in plants (cf. Phytochemistry Rev., 2, 371-390 (2003)).

Representative lignans include (+)-sesamin, (+)-sesaminol, (+)-sesamolin, (+)-pinoresinol, (+)-piperitol and (+)-sesamolinol contained in sesame (*Sesamum indicum*); (+)-pinoresinol, (−)-arctigenin and (−)-matairesinol contained in *Forsythia intermedia*; (−)-pinoresinol and (−)-lariciresinol contained in *Daphne tangutica*; (+)-secoisolariciresinol contained in *Linum usitatissimum*; etc. Molecular structures of these lignans are diverse (cf. Wood Research, 90, 27-110 (2003), etc.). Sesame lignans typified by (+)-pinoresinol are classified into furofuran lignans identified in the widest variety of plant species. Sesamin, which is one of the sesame lignans, displays an abundance of biological activities and are effective for improving cholesterol metabolism, liver function and immune function (see, e.g., Goma: SONO-KA-GAKU-TO-KINOSEI (Sesame: Science and Function), edited by Mitsuo Namiki, Maruzen Planet Publishing Co. (1998)). Methods for the separation and purification of sesamin from sesame seeds or sesame lees have already been launched (see, e.g., Japanese Patent Laid-open Publication (Kokai) No. 2001-139579 and Japanese Patent Laid-open Publication (Kokai) No. 10-7676, and sesamin-based liver function improving/potentiating agents having an alcoholysis-promoting activity are commercially available (trade name: Sesamin, from sales agency Suntory, Ltd.). It is reported that lignans other than sesamin (see, e.g., sesaminol, sesamolin, etc.) also have biological activities (see, e.g., J. Bioscience, Biotechnology and Biochemistry, 76: 805-813 (2002)). As such, lignans or their derivatives are useful as physiologically active substances having various physiological activities or their intermediates.

Hereinafter, the polynucleotide encoding the polypeptide of the present invention, which has the lignan methylation activity, and the polynucleotide encoding the polypeptide as well as their utilization are described in detail.

(1) Polynucleotide

First, the present invention provides the polynucleotide as defined in any one of (a) to (d) below:

(a) a polynucleotide comprising a polynucleotide consisting of the nucleotide sequence of SEQ ID NO: 1 or 3;

(b) a polynucleotide comprising a polynucleotide encoding a protein consisting of the amino acid sequence of SEQ ID NO: 2 or 4;

(c) a polynucleotide, which hybridizes to a polynucleotide consisting of a part or the whole of a nucleotide sequence complementary to the nucleotide sequence of SEQ ID NO: 1 or 3 under high stringent conditions and encodes a protein having an activity of transferring a methyl group to a lignan; and, (d) a polynucleotide comprising a polynucleotide encoding a protein consisting of the amino acid sequence of SEQ ID NO: 2 or 4 wherein one or more amino acids are deleted, substituted, inserted and/or added and having an activity of transferring a methyl group to a lignan.

As used herein, the term "polynucleotide" is interchangeably used with "gene," "nucleic acid" or "nucleic acid molecule," and is intended to mean a polymeric form of nucleotides. As used herein, the term "base sequence" is interchangeably used with "nucleic acid sequence" or "nucleotide sequence," and is given as the sequence of deoxyribonucleotides (abbreviated as A, G, C and T).

The polynucleotide of the present invention can be present in the form of RNA (e.g., mRNA) or DNA (e.g., cDNA or genomic DNA). The DNA may be double-stranded or single-stranded. Single-stranded DNA or RNA may be a coding strand (also known as a sense strand), or it may be a non-coding strand (also referred to as an anti-sense strand).

As used herein, the term "oligonucleotide" is intended to mean linked nucleotides of, e.g., several to several tens (e.g., 2 to 60) and interchangeably used with "polynucleotide." In the oligonucleotide, a short string of nucleotides is called a dinucleotide (dimer) or a trinucleotide (trimer), and a long string of nucleotides is expressed by the number of nucleotides polymerized, such as a 30-mer or a 100-mer. The oligonucleotide may be produced as a fragment of longer polynucleotide or chemically synthesized.

As used herein, the term "fragment of the polynucleotide" is intended to mean a fragment of the polynucleotide having at least 12 nt (nucleotides), preferably about 15 nt, more preferably at least about 20 nt, much more preferably at least about 30 nt and most preferably at least about 40 nt, in length. By the "fragment of at least 20 nt in length," it is intended to mean a fragment containing consecutive 12 or more nucleotides derived from the nucleotide sequence represented by, for example, SEQ ID NO: 1. By referring to the specification, the nucleotide sequence represented by SEQ ID NO: 1 is provided and one skilled in the art can easily produce a DNA fragment based on SEQ ID NO: 1. For instance, digestion with a restricted endonuclease or ultrasonic shear can be readily used to prepare fragments with various sizes. Alternatively, such fragments can be prepared synthetically. Appropriate fragments (oligonucleotides) are synthesized on an Applied Biosystems Incorporated (ABI, 850 Lincoln Center Dr., Foster City, Calif. 94404) Model 392 synthesizer, etc.

The polynucleotide of the present invention encodes a polypeptide having the lignan methylation activity. Such a polynucleotide is typically a polynucleotide comprising a polynucleotide consisting of the nucleotide sequence of SEQ ID NO: 1 or 3; or a polynucleotide comprising a polynucleotide encoding a protein consisting of the amino acid sequence of SEQ ID NO: 2 or 4. Preferably, the polynucleotide of the present invention is a polynucleotide having the nucleotide sequence of SEQ ID NO: 1 or 3 or a polynucleotide encoding a polypeptide having the amino acid sequence of SEQ ID NO: 2 or 4.

The polynucleotide of the present invention may be a variant having the nucleotide sequence of SEQ ID NO: 1 or 3, wherein one or more (e.g., 1 to 30, 1 to 20, 1 to 10, 1 to several (e.g., 6), 1 to 5, 1 to 3, or 1 to 2) nucleotides are deleted, inserted, substituted, and/or added, so long as the polypeptide encoded by the polynucleotide has the lignan methylation activity. The variant may be altered in coding regions, non-coding regions, or both regions. Alterations in the coding regions may generate conservative or non-conservative amino acid deletions, insertions, substitutions or additions.

The polynucleotide of the present invention includes a polynucleotide, which encodes a polypeptide having the lignan methylation activity and hybridizes to a polynucleotide consisting of the nucleotide sequence complementary to the nucleotide sequence of SEQ ID NO: 1 or 3 under stringent hybridization conditions.

Hybridization can be performed by such a well-known method as described in Sambrook et al., Molecular Cloning, A Laboratory Manual, 2nd Ed., Cold Spring Harbor Laboratory (1989). Higher temperature and lower salt concentration normally result in higher stringency (difficulty in hybridization) so that a more homologous polynucleotide can be obtained. Appropriate temperature for the hybridization varies depending upon nucleotide sequence or length of the nucleotide sequence. Where a DNA fragment consisting of 18 bases encoding 6 amino acids is used as a probe, the temperature is preferably 50° C. or lower.

As used herein, the term "stringent hybridization conditions" is intended to mean incubation at 42° C. overnight in a hybridization solution (50% formamide, 5×SSC (150 mM NaCl and 15 mM trisodium citrate), 50 mM sodium phosphate (pH 7.6), 5×Denhardt's solution, 10% dextran sulfate and 20 μg/ml of denatured sheared salmon sperm DNA), followed by washing the filter in 0.1×SSC at about 65° C. By a polynucleotide which hybridizes to a "part" of the polynucleotide, it is intended to mean a polynucleotide (either DNA or RNA) which hybridizes to at least about 15 nucleotides (nt), and more preferably at least about 20 nt, still more preferably at least about 30 nt, and even more preferably about 30-70 nt of the reference polynucleotide.

The present invention further provides the polynucleotide consisting of the nucleotide sequence which is identical by at least 80%, preferably at least by 85%, 90%, 92%, 95%, 96%, 97%, 98% or 99%, to the nucleotide sequence of SEQ ID NO: 1 or 3.

Whether any arbitrary particular nucleic acid molecule is identical by at least 80%, 85%, 90%, 92%, 95%, 96%, 97%, 98% or 99% with, e.g., the nucleotide sequence of SEQ ID NO: 1 or 3 can be determined by using known computer programs (e.g., the Bestfit program (Wisconsin Sequence Analysis Package, Version 8 for Unix (registered trademark), Genetics Computer Group, University Research Park, 575 Science Drive, Madison, Wis. 53711). The Bestfit uses the local homology algorithm of Smith and Waterman to find the best segment of homology between two sequences (Advances in Applied Mathematics, 2: 482-489 (1981)). Using the Bestfit or any other sequence alignment program to determine whether a particular sequence is, e.g., 95% identical with the reference nucleotide sequence in accordance with the present invention, the parameters are set in such a manner that the percentage of identity is computed over the full length of the reference nucleotide sequence and gaps in homology of up to 5% of the total number of nucleotides in the reference sequence are allowed.

In a specific embodiment, the identity (also termed as a global sequence alignment) between a reference (QUERY) sequence (the sequence in accordance with the present invention) and a target sequence is determined by using the FASTDB computer program based on the algorithm of Brutlag, et al. (Comp. App. Biosci., 6: 237-245 (1990)). Preferred parameters used in the FASTDB alignment of DNA sequences to calculate the identity percentage are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the target nucleotide sequence (whichever is shorter).

The present invention further includes an oligonucleotide consisting of a fragment of the polynucleotide described above or its complementary sequence. Even where the oligonucleotide of the present invention does not encode the lignan methylation polypeptide, one skilled in the art readily understands that the polynucleotide of the present invention can be used as a primer for polymerase chain reaction (PCR) to produce the polypeptide of the present invention. Another use of the oligonucleotide of the present invention which does not encode the lignan methylation polypeptide includes the following: (1) isolation of the lignan methyltransferase genes from a cDNA library or its allelic variants or splicing variants; (2) in situ hybridization (e.g., "FISH") to metaphase chromosomal spreads to provide the precise chromosomal location of the lignan methyltransferase genes (as described in Verma, et al., Human Chromosomes: A Manual of Basic Techniques, Pergamon Press, New York (1988)); and (3) northern blot analysis for detecting the expression of lignan methyltransferase mRNA in particular tissues.

The polynucleotide or oligonucleotide of the present invention can be used as a tool for gene expression manipulation by an antisense RNA mechanism. By means of the antisense RNA technique, a decrease of the gene product from the endogenous gene is observed. By introducing the oligonucleotide of the present invention, the level of the polypeptide having the lignan methylation activity can be reduced and hence the content or content ratio of the methylated lignans in a plant can be controlled (increased or decreased). The polynucleotide or oligonucleotide of the present invention may be those having a sequence from the untranslated region (UTR), a sequence from vector sequences (including expression vector sequences), etc.

The method for acquiring the polynucleotide or oligonucleotide of the present invention includes various known techniques for isolating DNA fragments containing the polynucleotide or oligonucleotide of the present invention. For instance, a probe specifically hybridizing to a part of the nucleotide sequence of the polynucleotide of the present invention is prepared, followed by screening of a genomic DNA library or cDNA library. Such a probe may be a polynucleotide (oligonucleotide) which specifically hybridizes at least to a part of the nucleotide sequence of the polynucleotide of the present invention or its complementary sequence.

These polynucleotides as screened by the hybridization are naturally occurring polynucleotides (e.g., polynucleotides derived from plants such as plants of the Pedaliaceae, Bryophyta, etc.) but may also be polynucleotides derived from other than plants.

An alternative method of acquiring the polynucleotide of the present invention further includes a method using PCR. This PCR amplification method involves, e.g., the step of preparing primers using the 5'-end and/or 3'-end sequences (or their complementary sequences) of cDNA of the polynucleotide of the present invention and the step of amplifying by PCR using these primers as the template of genomic DNA (or cDNA), etc. By using this method, DNA fragments containing the polynucleotide of the present invention can be acquired in large quantities.

Supply sources to acquire the polynucleotide of the present invention preferably include, but are not particularly limited to, biological materials containing piperitol or pinoresinol. As used herein, the term "biological material" is intended to mean a biological sample (a tissue sample or cell sample obtained from an organism). In EXAMPLES later described, sesame is employed but not limited thereto.

By using the polynucleotide of the present invention, the polypeptide having the lignan methylation activity can be synthesized in transformants or cells. By using the polynucleotide of the present invention, an organism which expresses the polypeptide having the lignan methylation activity can be readily detected by detecting the hybridizing polynucleotide.

The oligonucleotide of the present invention can be used as a hybridization probe to detect the polynucleotide encoding the polypeptide having the lignan methylation activity or as a primer to amplify said polynucleotide, whereby the organism or tissue expressing the polypeptide having the lignan methylation activity can be easily detected. Moreover, by using the aforesaid oligonucleotide as an antisense oligonucleotide, expression of the polypeptide having the lignan methylation activity can be repressed in the organism described above, or its tissues or cells.

(2) Polypeptide

The present invention also provides the protein (polypeptide) encoded by the polynucleotide of the present invention described above. Such a polypeptide is typically a protein consisting of the amino acid sequence of SEQ ID NO: 2 or 4.

As used herein, the term "polypeptide" is interchangeably used with "peptide" or "protein." The "fragment" of the polypeptide is intended to mean a partial fragment of the polypeptide. The polypeptide of the present invention may be isolated from natural supply sources or may be chemically synthesized.

The polypeptide of the present invention includes a naturally occurring purified product, a chemically synthesized product, and a product produced from prokaryotic hosts or eukaryotic hosts (including, e.g., bacterial cells, yeast cells, higher plant cells, insect cells and mammal cells) using recombinant techniques. Depending upon the host used in a recombinant production protocol, the polypeptide of the present invention may be glycosylated or non-glycosylated. In some cases, the polypeptide of the present invention may further contain an initially modified methionine residue, as a result of a host-mediated process.

The present invention still further provides the polypeptide having the lignan methylation activity. As used herein, the "lignan methylation activity" is intended to mean the activity to methylate lignans, namely, the activity to transfer a methyl group to lignans. In other words, "methyltransferase" and "enzyme transferring a methyl group" are interchangeably used throughout the specification. The "lignan methylation activity" can be assayed or confirmed by reacting methyl donor SAM and substrate lignan with lignan methyltransferase and analyzing the reaction product by HPLC or LC-MS. A general method for assaying the methyltransferase activity is described in known literatures (publications: Toquin, V., et al. (2003) Plant Mol. Biol., 52, 495-509., Gang, D. R., et al. (2002) Plant Cell, 14, 505-519).

The polypeptide of the present invention also includes variants of the polypeptide consisting of the amino acid sequence of SEQ ID NO: 2 or 4 and having the lignan methylation activity.

Such variants include proteins consisting of the amino acid sequence of SEQ ID NO: 2 or 4, wherein one or more (e.g., 1 to 30, 1 to 20, 1 to 10, 1 to several (6), 1 to 3, 1 to 2, etc.) amino acids (amino acid residues) are deleted, substituted, inserted and/or added, and having the activity to transfer a methyl group to lignans. The "deletion, substitution, insertion and/or addition" includes inversion, repetition and type substitution (e.g., substitution of another residue for a hydrophilic residue; normally, a strongly hydrophilic residue is not substituted for a strongly hydrophobic residue, however). In particular, "neutral" amino acid substitution in the polypeptide very little affects the activity of the polypeptide in general.

It is well known in the art that some amino acids in the amino acid sequence of the polypeptide may be easily modified without any significant effect on the structure or function of this polypeptide. It is also well known that not only in artificially modified ones but also in naturally occurring proteins, there are variants which do not significantly alter the structure or function of the protein.

One skilled in the art can easily modify one or more amino acids in the amino acid sequence of the polypeptide by applying well-known techniques. For example, an optional nucleotide in the polynucleotide encoding the polypeptide can be varied by known point mutagenesis methods. Further by designing primers corresponding to optional sites of the polynucleotide encoding the polypeptide, deletion variants or addition variants can be prepared. Furthermore, whether the prepared variants have the desired activity can be easily assayed by using the methods described in the specification.

Preferred variants contain conservative or non-conservative amino acid substitutions, deletions or additions, which are preferably silent substitutions, additions and deletions, and particularly preferably conservative substitutions. These variants do not change the activity of the polypeptide of the present invention.

The conservative substitution considered to be representative includes replacement of another amino acid for one amino acid in aliphatic amino acids Ala, Val, Leu and Ile; exchange of the hydroxyl residues Ser and Thr, exchange of the acidic residues Asp and Glu, replacement between the amide residues Asn and Gln, exchange of the basic residues Lys and Arg, and replacement between the aromatic residues Phe and Tyr.

As described above in detail, a further guidance about which amino acid alteration could be phenotypically silent (namely, which amino acid alteration could hardly exert significantly harmful effects on the function) can be found in Bowie, J. U., et al., "Deciphering the Message in Protein Sequences: Tolerance to Amino Acid Substitutions," Science 247: 1306-1310 (1990).

As described above, these variant polypeptides are not limited to polypeptides having artificially induced variations by publicly known variant polypeptide production processes but may also be those isolated and purified from naturally occurring polypeptides.

The polypeptide of the present invention may be any polypeptide wherein the amino acids are linked through the peptide bond, but is not limited thereto and may also be a conjugated polypeptide having a structure other than the polypeptide. As used herein, the "structure other than the polypeptide" includes a sugar chain, an isoprenoid group, etc. but is not particularly limited thereto.

The polypeptide of the present invention may contain an additional polypeptide. The additional polypeptide includes a polypeptide tagged with an epitope such as His, Myc, Flag, etc.

Also, the polypeptide of the present invention may be in such a state that the polynucleotide encoding the polypeptide of the present invention is introduced into a host cell and its polypeptide is intracellularly expressed, or may be isolated and purified from cells, tissues, etc.

The polypeptide of the present invention can be produced by recombination or chemically synthesized as described below in detail (see, e.g., Houghten, R. A., Proc. Natl. Acad. Sci. USA 82: 5131-5135 (1985); U.S. Pat. No. 4,631,211, etc.).

The polypeptide of the present invention can catalyze the methylation of lignans (especially pinoresinol or piperitol).

(3) Use of the Polypeptide or Polynucleotide of the Invention

The present invention further provides the method of controlling (increasing or decreasing) the amounts of lignans and methylated lignans in organisms (preferably plants) by using the polypeptide or polynucleotide of the present invention, as well as use of the controlled organisms (preferably plants).

(A) Vector

The present invention provides a vector which is used to produce the polypeptide having the lignan methylation activity. The vector of the present invention may be a vector used for in vitro translation or a vector used for recombinant expression.

The vector of the present invention is not particularly limited, so long as the vector carries the polynucleotide of the present invention. The vector includes, for example, a recombinant expression vector inserted with cDNA of the polynucleotide encoding the polypeptide having the lignan methylation activity, and the like. A method for producing the recombinant expression vector includes a method which comprises using a plasmid, phage or cosmid, etc., but is not particularly limited thereto.

The vector is not particularly limited to specific kinds but may be appropriately chosen such that it can be expressed in host cells. In other words, a promoter sequence is appropriately chosen to ensure the expression of the polynucleotide of the present invention depending upon kind of host cells, and this promoter and the polynucleotide of the present invention are incorporated into various plasmids, etc., and then the vectors thus obtained may be used as expression vectors.

The expression vector of the present invention contains expression controlling regions (e.g., promoter, terminator and/or a replication origin, etc.) depending upon a biological species of the host to be introduced. As the promoter for bacteria, there are employed conventional promoters (e.g., a trc promoter, a tac promoter, a lac promoter, etc.). As the promoter for yeast, a glyceraldehyde 3-phosphate dehydrogenase promoter, a PHO5 promoter, etc. may be used. The promoter for filamentous fungi includes, for example, promoters of amylase, trp C, etc. The promoter for animal cell hosts includes viral promoters (e.g., SV40 early promoter, SV40 late promoter, etc.). The recombinant expression vector used to transform the plant is not particularly limited as far as the vector is capable of expressing the polynucleotide of the present invention in said plant. Examples of such vectors include a vector bearing a promoter capable of constitutively expressing the polynucleotide in plant cells (e.g., a 35S promoter of cauliflower mosaic virus) in plant cells, and a vector inducibly activated by external stimulation.

The expression vector may be prepared in a conventional manner using restriction enzymes and/or ligases, etc. The host cells may be transformed with the expression vector in a conventional manner.

The host transformed using the expression vector described above is incubated, cultivated or raised. Thereafter the objective protein can be recovered and purified from the culture or the like in a conventional manner (e.g., filtration, centrifugation, disruption of cells, gel filtration chromatography, ion exchange chromatography, etc.).

The expression vector preferably contains at least one selection marker. Such a marker includes a dihydrofolate reductase gene or neomycin resistance gene for eukaryotic cell culture and a tetracycline or ampicillin resistance gene for the culture in E. coli and other bacteria.

By using the selection marker described above, it can be confirmed whether or not the polynucleotide of the present invention is introduced into a host cell and further whether or not the polynucleotide is certainly expressed in a host cell. Alternatively, the polypeptide of the present invention may be expressed as a fused polypeptide (e.g., a fused polypeptide with GFP) and the GFP fluorescence may be used as a marker.

(B) Transformant or Cell

The present invention provides transformants or cells in which the polynucleotide encoding the polypeptide having the lignan methylation activity described above is introduced. As used herein, the term "transformant" is intended to mean not only a tissue or organ but also an individual organism.

Methods of preparing (producing) transformants or cells are not particularly limited, and include, for example, the aforesaid method which involves transformation through incorporation of a recombinant vector into a host. The host cells used herein are not particularly limited and various cells heretofore known may be advantageously used. Specific examples include, but not limited to, bacteria such as *Escherichia coli*, etc., yeasts (*Saccharomyces cerevisiae, Schizosaccharomyces pombe*), *Caenorhabditis elegans* or oocytes of *Xenopus laevis*, etc. Culture media and conditions suitable for the host cells described above are well known in the art. Organisms to be transformed are not particularly limited, and examples include various microorganisms, plants or animals illustratively given for the host cells described above.

The transformants or cells of the present invention are characterized in that their compositions are altered from those in naturally occurring lignans and/or methylated lignans. The transformants or cells of the present invention are preferably plants or their progeny, or tissues derived therefrom, more preferably, sesame, Forsythia intermedia or *Linum* usitatissimum. In these transformants or cells, the content of methylated lignans in organisms, which produce lignans, can be increased or decreased by the method of controlling the contents of methylated lignans of the present invention.

The transformant of the present invention can be a plant transformant. The plant transformant in accordance with this embodiment can be acquired by introducing a recombinant vector bearing the polynucleotide of the present invention into a plant in such a manner that the polypeptide encoded by the said polynucleotide can be expressed.

Where a recombinant expression vector is used, the recombinant expression vector used to transform the plant is not particularly limited as far as the vector is capable of expressing the polynucleotide of the present invention in said plant. Examples of such vectors include a vector bearing a promoter capable of constitutively expressing the polynucleotide in plant cells (e.g., a 35S promoter of cauliflower mosaic virus) in plant cells, and a vector inducibly activated by external stimulation.

Plants which are to be the target of transformation in the present invention may be any of entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or various types of plant cells (e.g., suspension culture cells), protoplasts, leaf slices, callus, and the like. Specific examples of plant species which are used for transformation include, but are not limited to, those belonging to the Monocotyledoneae or the Dicotyledoneae.

For transformation of genes into plants, conventional transformation methods known to one skilled in the art (e.g., the *Agrobacterium* method, gene gun, the PEG method, the electroporation method, etc.) are used. For example, the *Agrobacterium*-mediated method and the method of directly introducing into plant cells are well known. When the *Agrobacterium* method is used, the constructed plant expression vector is introduced into an appropriate *Agrobacterium* strain (e.g., *Agrobacterium tumefaciens*), followed by infection of aseptically cultured leaf discs with this strain according to the leaf disc method (Hirobumi Uchimiya, Manuals for Plant Gene Manipulation (1990), 27-31, Kodansha Scientific Co., Ltd., Tokyo). Thus, the transgenic plant can be obtained. In addition, the method of Nagel, et al. (Micribiol. Lett., 67, 325 (1990)) may be used. This method involves introducing first, e.g., an expression vector into *Agrobacterium* and then introducing the transformed *Agrobacterium* into plant cells or plant tissues according to the method described in Plant Molecular Biology Manual (S. B. Gelvin, et. al., Academic Press Publishers). Herein, the "plant tissue" includes callus, which is obtained by culturing plant cells. When the transformation is carried out using the *Agrobacterium* method, binary vectors (pBI121 or pPZP202, etc.) can be used.

For direct transfer of genes into plant cells or plant tissues, the electroporation method and the gene gun method are known. When the gene gun is used, entire plant bodies, plant organs or plant tissues per se may be used, or may be used after preparation of protoplasts. The samples thus prepared can be bombarded using a gene transfer apparatus (e.g., PDS-1000 (BIO-RAD, Inc.), etc.). Bombardment conditions vary depending upon type of the plant or sample. Normally, the sample is bombarded under a pressure of about 450-2000 psi at a distance of 4-12 cm.

The cells or plant tissues in which the gene is introduced are first selected by chemical resistance such as hygromycin resistance, etc. and then regenerated into plant bodies in a conventional manner. Regeneration of plant bodies from the transformant cells can be performed by methods known to one skilled in the art, depending upon kind of plant cells.

Where a plant culture cell is used as a host, transformation is preformed by introducing the recombinant vector into culture cells by the gene gun method, the electroporation method, etc. Callus, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

Whether or not the gene is introduced into the host can be confirmed by PCR, Southern hybridization, northern hybridization, or the like. For example, DNA is prepared from the transgenic plant and DNA-specific primers are then designed for PCR.

Once the transgenic plant wherein the polynucleotide of the present invention is incorporated into the genome is acquired, its progeny can be obtained by sexual or asexual reproduction of the plant body. Also, the plant body can be mass-produced by acquiring from the plant body or its progeny or clones thereof, e.g., seeds, fruits, cut panicles, tubers, tuberous roots, strains, callus, protoplasts, etc., and then using them as the origin. Accordingly, the present invention also encompasses the plant body in which the polynucleotide of the present invention is expressibly introduced, or progenies of the plant body having the same property as in the plant body, and tissues derived therefrom.

Moreover, the transformation methods for various plants are already reported. Examples of transformable plants may include, but not be limited to, sesame, rice plant, tobacco, barley, wheat, rapeseed, potato, tomato, poplar, banana, eucalyptus, sweet potato, soybean, alfalfa, lupinus, corn, cauliflower, rose, chrysanthemum, carnation, snapdragon, cyclamen, orchid, Prairie gentian, freesia, gerbera, gladiolus, gypsophila, kalancoe, lily, pelargonium, geranium, petunia, torenia, tulip, Forsythia intermedia, *Arabidopsis thaliana, Linum usitatissimum, Lotus japonicus*, and so on.

In a preferred embodiment, the transformant of the present invention can be prepared using sesame. The method of preparing the transformant of sesame includes such a known method as described in, for example, T. Asamizu: Transformation of sesame plants using MAT vector system: introduction of fatty acid desaturase genes, Sesame Newsletter, 16: 22-25 (2002).

By using the transgenic sesame thus obtained, the methylated lignans are produced in the sesame. Therefore, the methylated lignans (piperitol and/or pinoresinol) can be produced at low costs by an environment-friendly production process.

In another preferred embodiment, a tobacco plant can be used preferably as the transformant of the present invention. Like petunia the tobacco plant is a typical plant which readily undergoes transformation and is capable of regenerating from a cell wall-removed single cell (protoplast) to a single plant body. This single plant body regenerated does not result in a chimeric pattern unlike the single body derived from multiple cells so that its transformants can be efficiently produced.

A preferred example of the transformation method for tobacco is the leaf disc method. According to this method, operations are easy and multiple independent transformants can be obtained from a single leaf disc. The transformation method is described in, e.g., "SHIN-SEIBUTSU KAGAKU JIKKEN-NO-TEBIKI (New Guidance of Biochemical Experiment) 3: Isolation/Analysis of Nucleic Acid and Gene Research Method, published by Kagaku Dojin, 1996."

By using the transgenic tobacco thus obtained, the lignan methyltransferase can be produced at low costs by an environment-friendly production process.

In yet another preferred embodiment, a rice plant can be advantageously employed as the transformant of the present invention. By using the transgenic rice plant, the lignan methyltransferase can be produced in the rice plant at low costs by an environment-friendly production process.

Where an organism contains lignans (especially pinoresinol or piperitol), irrespective of the species of organism, the transformant of the present invention can produce the methylated lignans by introducing the aforesaid polynucleotide therein.

When the transformant wherein a recombinant expression vector bearing the polynucleotide encoding the polypeptide of the present invention is introduced is used, the transformant can catalyze the reaction to methylate endogenous lignans present in organisms such as plants. Thus, the methylated lignans can be mass-produced at low costs by an environment-friendly production process. In addition, the present invention can provide inexpensive foodstuff or industry products through the methylated lignans mass-produced.

By using the transformant of the present invention, the polypeptide which catalyzes the lignan methylation can be provided at low costs under environment-friendly conditions.

In an embodiment, the cells in accordance with the present invention may be a variety of bacterial cells. The cells in accordance with this embodiment are obtained by introducing a recombinant vector bearing the polynucleotide of the present invention in cells in such a manner that the polypeptide encoded by the polynucleotide can be expressed.

According to the disclosure in the specification, one skilled in the art can readily understand that once a recombinant expression vector bearing the polynucleotide encoding the polypeptide having the lignan methylation activity is transduced, the lignan methylation capability can be imparted to organisms over a wide range from bacteria to higher plants.

When an organism contains lignans (especially pinoresinol or piperitol), irrespective of the species of organism, the cells can produce the methylated lignans by introducing the aforesaid polynucleotide therein.

When the cells wherein a recombinant expression vector bearing the polynucleotide encoding the polypeptide of the present invention is used, the lignan methylation reaction can be catalyzed within the cells. Thus, the methylated lignans can be mass-produced at low costs by an environment-friendly production process. In addition, the present invention can provide inexpensive foodstuffs or industry products through the mass-production of methylated lignans.

By using the cells of the present invention, the polypeptide which catalyzes the lignan methylation reaction can be provided at low costs under environment-friendly conditions.

(C) Method for Producing Polypeptide

The present invention provides the method for producing the polypeptide of the present invention. By using the method for producing the polypeptide of the present invention, the polypeptide which catalyzes the lignan methylation reaction can be provided at low costs under environment-friendly conditions. Further by using the method for producing the polypeptide of the present invention, the polypeptide which catalyzes the lignan methylation reaction can be readily produced.

According to the method for producing the polypeptide of the present invention, the vector bearing the polynucleotide encoding the polypeptide of the present invention can be used.

It is preferred to use the vector described above in a cell-free protein synthesis system. Where the cell-free protein synthesis system is used, various commercially available kits may be employed. Preferably, the method for producing the polypeptide in this embodiment comprises the step of incubating the vector described above and a cell-free protein synthesis solution.

According to the method for producing the polypeptide in accordance with this embodiment, a recombinant expression system can be used as well. Where the recombinant expression system is used, there may be adopted a method which involves incorporating the polynucleotide of the present invention into a recombinant expression vector, introducing the vector expressibly into a host by known methods, translating in the host and purifying the resulting polypeptide described above; and so on. The recombinant expression vector may or may not be a plasmid, so long as the objective polynucleotide can be introduced into a host. Preferably, the method for producing the polypeptide in this embodiment includes the step of introducing the vector described above into a host.

Prokaryotes or eukaryotes may be used as hosts. As the prokaryotic host, bacteria belonging to, for example, the genus *Escherichia* (e.g., *Escherichia coli*, etc.), bacteria belonging to, for example, the genus *Bacillus* (e.g., *Bacillus subtilis*, etc.) may be used. As the eukaryotic host, lower eukaryotes (e.g., eukaryotic microorganisms such as yeast, filamentous fungi, etc.). The yeast includes microorganisms belonging to the genus *Saccharomyces* (e.g., *Saccharomyces cerevisiae*, etc.) and the filamentous fungi include microorganisms belonging to the genus *Aspergillus* (e.g., *Aspergillus oryzae, Aspergillus niger*, etc.), and microorganisms belonging to the genus *Penicillium*. Animal cells or plant cells may also be used as hosts. The animal cells include cells from mice, hamsters, monkeys, humans, etc. In addition, insect cells (e.g., silkworm cells or silkworm imagines) may also be used as hosts.

The host cells described above are not particularly limited and various cells heretofore known may be advantageously used. Specific examples include, but not limited to, bacterial such as *Escherichia coli*, etc., yeasts (*Saccharomyces cerevisiae, Schizosaccharomyces pombe*), *Caenorhabditis elegans* or oocytes of *Xenopus laevis*, etc. Culture media and conditions suitable for the host cells described above are well known in the art.

Where an exogenous polynucleotide is introduced into a host as described above, preferably the expression vector has a promoter having incorporated therein to function in a host so as to express the exogenous polynucleotide. Though methods for purification of the polypeptide recombinantly produced are different depending upon host used and property of the polypeptide, the target polypeptide can be purified relatively easily by using a tag, etc.

Preferably, the method for producing the polypeptide in accordance with this embodiment further comprises the step of purifying the aforesaid polypeptide from the extract of cells or tissues having the polypeptide of the present invention. The step of purifying the polypeptide preferably comprises, but is not limited to, preparing a cell extract from cells or tissues by well-known methods (e.g., a method which comprises disrupting cells or tissues, centrifuging and recovering soluble fractions), followed by purification from the cell extract by well-known methods (e.g., ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography). Most preferably, high performance liquid chromatography ("HPLC") is employed for purification.

The polypeptide of the present invention can be prepared by purifying said polypeptide from cells or tissues naturally expressing the polypeptide of the present invention, or by chemical synthesis.

Methods of producing the variant polypeptide are not particularly limited. The variant polypeptide can be produced by well known methods of producing variant polypeptide, for example, site-specific mutagenesis (see, e.g., Hashimoto-Gotoh, Gene, 152, 271-275 (1995)), a method for producing variant polypeptide which involves introducing point mutations into nucleotide sequences using PCR, a method for producing mutants by transposon insertion, etc. Commercially available kits may also be used to produce the variant polypeptide.

As described above, the polypeptide of the present invention may be produced by known conventional techniques, at least, based on the amino acid sequence of the polypeptide having the lignan methylation activity, or based on the nucleotide sequence of the polynucleotide encoding the polypeptide having the lignan methylation activity.

(D) Method for Producing Methylated Lignan

So far, the production of lignans and methylated lignans has been relied on extraction from sesame and thus involves difficulties in mass production, etc. According to the present invention, lignans and methylated lignans can be mass-produced at low costs.

The present invention provides the method for producing methylated lignans using organisms or cells expressing the polypeptide of the present invention. The organisms described above may be naturally occurring intact organisms or transformants produced using the recombinant expression system. According to the method for producing methylated lignans, lignans (especially, pinoresinol or piperitol) can be produced efficiently.

In an embodiment, the method for producing methylated lignans of the present invention comprises producing the methylated lignans using the organism transformed with the polynucleotide encoding the polypeptide of the present invention or its tissues. Preferably, the organism described above includes the transgenic plants or cells described above, especially preferably, *Escherichia coli*, sesame, Forsythia intermedia or *Linum usitatissimum*.

The method for producing methylated lignans of the present invention comprises the step of introducing the polynucleotide encoding the polypeptide of the present invention into the organism described above. For the step of introducing the polynucleotide into the organism described above, the various gene transfer methods described above may be used.

In this aspect of the embodiment, the organism described above has different compositions between the methylated lignans produced before transformation and those produced after transformation. Specifically, the lignans and methylated lignans obtained from the organism described above provide an increased content of the lignans and methylated lignans. The method for producing the methylated lignans from this aspect of the embodiment preferably further comprises the step of extracting the methylated lignans from the organism described above.

The method for producing methylated lignans of the present invention comprises the step of introducing the oligonucleotide of the present invention as an antisense oligonucleotide into an organism which naturally expresses the polypeptide of the present invention. For the step of introducing the oligonucleotide into the organism described above, the antisense RNA technique described above may be used. Preferably, the method for producing methylated lignans in accordance with this embodiment further comprises the step of using the antibody or oligonucleotide described above to identify an organism capable of naturally expressing the polypeptide of the present invention. The method for producing methylated lignans in accordance with this aspect of the present embodiment further comprises the step of extracting the methylated lignans from the organism described above.

In this embodiment, the organism described above has different compositions between the methylated lignans produced before introduction of the oligonucleotide described above and those produced after the introduction. Specifically, the lignans and methylated lignans obtained from the organism described above provide a decreased content of the same.

(E) Foodstuff and Industrial Product

The present invention provides foodstuffs and industrial products using the methylated lignans, which are obtained by the method for producing the methylated lignans described above. The foodstuffs referred to in this section may be any of seeds, fruits, cut panicles, tubers and/or tuberous roots, etc. of the transgenic plants described above, or may be foodstuffs (e.g., sesame, Forsythia intermedia or *Linum usitatissimum*, or processed foodstuffs) manufactured using the methylated lignans extracted from the transgenic plant described above. The foodstuffs or industrial products of the present invention may contain a desired amount of lignans (especially, pinoresinol or piperitol).

For example, the solutions obtained by extracting methylated lignans from the transgenic plant of the present invention, in which the content of methylated lignans is increased as described above, can be provided as methylated lignan-rich foodstuffs. In addition to the methylated lignans extracted, the seeds, fruits, cut panicles, tubers and/or tuberous roots, etc. of the transgenic plants described above can also be provided as methylated lignan-rich foodstuffs. The target for alteration of the methylated lignan composition is not particularly limited but all organisms including animals, bacteria, yeasts, etc. may be targeted, in addition to plants.

Based on unique physical properties of the lignans and methylated lignans, the polypeptides or polynucleotides of the present invention are also available as raw materials for industrial products (e.g., industrial products such as films, biodegradable plastics, functional fibers, lubricants or detergents).

In the specification, the lignan methylation polypeptide of sesame is illustratively given as an example but it is obvious to one skilled in the art that the present invention should not be limited to the sesame-derived polypeptide or polynucleotide and relates to all polypeptides having the lignan methylation activity and use thereof. Lignan methyltransferases may be those derived from any one of plants, animals or microorganisms and can regulate the lignan content, so long as they possess the lignan methylation activity. The present invention further relates to a plant prepared by introducing the polynucleotide encoding the lignan methyltransferase, its progeny, or tissues thereof, in which the lignan content is controlled. The form of plant may also be a cut flower. By using the lignan methylation polypeptide of the present invention, production of the methylated lignans can be promoted or suppressed. One skilled in the art can readily understand that by using conventional procedures, it is possible to introduce the polynucleotide described above into plants and express the polynucleotide in a constitutive or tissue-specific manner, thereby increasing the expression of the target polypeptide, while it is also possible to repress the expression of the target polypeptide, using the antisense method, the cosuppression method, the RNAi method, etc.

EXAMPLES

The present invention will be described in more detail by referring to the following EXAMPLES but is not deemed to be limited thereto.

Molecular biological strategies used in EXAMPLES were implemented following the method described in WO 2004/018682 (PCT/JP03/10500) or Molecular Cloning (Sambrook et al., Cold Spring Harbour Laboratory Press, 1989), unless otherwise indicated in detail.

Example 1

EST Analysis of Sesame Seed

In the sesame seed-derived cDNA library described in a known literature (WO 2005/030944), pBK-CMV phagemid (Stratagene) was excised using the Rapid Excision Kit (Stratagene) according to the protocol recommended by the manufacturer, and infected into *Escherichia coli*. From the *Escherichia coli* colonies containing this sesame seed-derived ES, 5000 clones were picked up at random, and colony PCR was performed under the following conditions using M13RV primer (SEQ ID NO: 5) and M4 (−20) primer (SEQ ID NO: 6). The *Escherichia coli* colony was suspended in a mixture of 1× Ex-Taq buffer (TaKaRa), 0.2 mM dNTPs, 0.2 pmol/µl of each primer and 1.25U Ex-Taq polymerase, and PCR amplification was performed, after 5 minutes at 94° C., using 30 cycles of 1 minute at 94° C., 1 minute at 55° C. and 2 minutes at 72° C., followed by maintaining at 72° C. for 7 minutes.

```
SEQ ID NO: 5: M13RV: 5'-CAGGAAACAGCATTGAC

SEQ ID NO: 6: M4-20: 5'-GTAAAACGACGGCCAGT
```

These PCR products were applied to agarose gel electrophoresis and confirmed by ethidium bromide staining that EST contained in pBK-CMV was specifically amplified. After 4 µl each of these 5000 PCR products was mixed with 10 units of exonuclease I (USB) and 2 units of shrimp alkaline phosphatase (USB), the mixture was maintained at 37° C. for 30 minutes and then 80° C. for 20 minutes to terminate the enzyme reaction. Using 1 µl of this enzyme reaction solution, direct sequencing was performed under the following conditions. The reaction solution for sequencing is composed of 1 µl of the enzyme reaction solution, 3 µl of 5× BigDye Sequencing Buffer ver. 3.1 (Applied Biosystems), 2 µl of BigDyeSequencing RR ver. 3.1 (Applied Biosystems), 1 µl of 1.6 pmol/µl M13RV primer and 13 µl of sterile water. For sequencing the reaction was performed, after 1 minute at 96° C., using 25 cycles of 10 seconds at 96° C., 5 seconds at 50° C. and 4 minutes at 60° C. The reaction solution for sequencing was prepared by the protocol recommended by the manufacturer using DyeEx96 (QIAGEN) and the nucleotide sequence was determined using Sequencer Model 3100 (Applied Biosystems).

The 5000 nucleotide sequences obtained were subjected to homology search using Blastx, and partial sequences of the two sesame methyltransferases (Sesamum indicum O-methyltransferase; hereinafter SiOMT) showing homology to the methyltransferase gene were identified. The conditions for Blastx analysis are as follows. Program: Blastx ver. 2.2.9, Database: nr, Genetic code: standard (1), Filter: LOW complexity, Expect: 10, Word size: 3, Matrix: BLOSUM62, Gap Costs: Existence 11, Extension 1.

Example 2

Expression Analysis of Sesame Methyltransferase Genes

To analyze expression patterns of the two genes SiOMT1 and SiOMT2 obtained by the EST analysis, RT-PCR was carried out on cDNA in each part of sesame described in a known literature (WO 2005/030944) under the following conditions.

The solution for PCR is composed of 1 µl of cDNA, 1× Ex-Taq buffer (TaKaRa), 0.2 mM dNTPs, 0.2 pmol/µl of each primer and 1.25 U Ex-Taq polymerase. PCR amplification was performed, after 5 minutes at 94° C., using 32 cycles of 1 minute at 94° C., 1 minute at 55° C. and 2 minutes at 72° C., followed by maintaining at 72° C. for 5 minutes. SiOMT1-FW (SEQ ID NO: 7) and SiOMT1-RV (SEQ ID NO: 8) as well as SiOMT2-FW (SEQ ID NO: 9) and SiOMT2-RV (SEQ ID NO: 10) were used as SiOMT1- and SiOMT2-specific primers. For comparing the SiOMT genes and the endogenous genes in the expression level, PCR was performed simultaneously on an internal standard gene. Specifically, PCR was carried out on sesame 18S ribosomal RNA gene (Accession No. AF169853) using Si18SrRNA-F primer (SEQ ID NO: 1) and Si18SrRNA-R primer (SEQ ID NO: 12).

```
SEQ ID NO: 7: SiOMT1-FW:
5'-TTGCCCCATGTCATTCAAGAT
SEQ ID NO: 8: SiOMT1-RV:
5'-AAAATTCAGACTTATAACGATACCAAA

SEQ ID NO: 9: SiOMT2-FW:
5'-TTAGAAAAACTCAATTCGTCTAAT
SEQ ID NO: 10: SiOMT2-RV:
5'-CCTACATCCACGACGGAATCCAAA

SEQ ID NO: 11: Si18SrRNA-FW:
5'-tatgcttgtctcaaagattaa
SEQ ID NO: 12: Si18SrRNA-RV:
5'-aacatctaagggcatcacaga
```

Figure 2:
Figure 2:
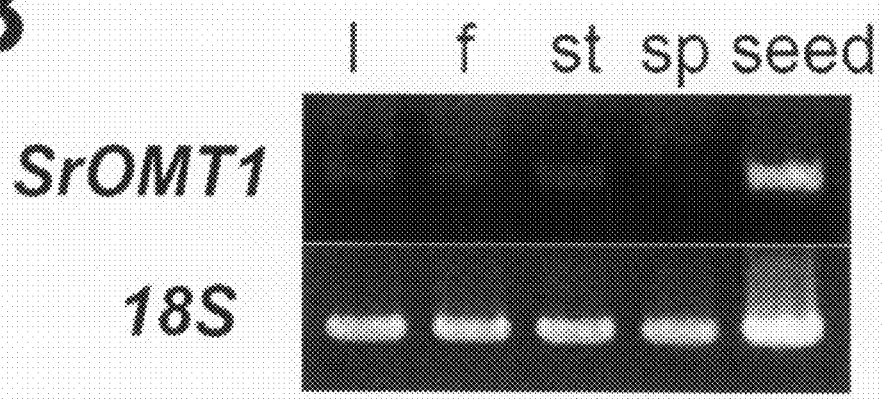

The PCR products were electrophoresed and stained with ethidium bromide. As a result, it was confirmed that the SiOMT genes (SiOMT1 and SiOMT2) were both strongly expressed in the seeds (FIG. 2-2A). In other words, it was confirmed that the expression regions of the two SiOMT genes coincided with the region where the methylated lignans were deposited.

Example 3

Cloning of Sesame Methyltransferase Genes

Since the both EST clones did not contain the 5' end of putative ORF, the 5' regions of respective SiOMT genes were amplified using the 5' rapid amplification of cDNA end (hereinafter 5' RACE) method. Specifically, each of the 5' regions was amplified using the following primers (SEQ ID NOS: 13-16) with GeneRacer kit (Invitrogen) according to the protocol recommended by the manufacturer.

```
SEQ ID NO: 13: GR-SiOMT1-RV:
5'-ccggcccactgttcgggtcctaacgggaaa

SEQ ID NO: 14: SiOMT1-NEST-RV:
5'-gcaaatccacttcataaaaat

SEQ ID NO: 15: GR-SiOMT2-RV:
5'-cctcgggttccgctctttctgctcccagaa

SEQ ID NO: 16: SiOMT2-NEST-RV:
5'-atcaatttgggaaattacaaa
```

In SiOMT2, the EST clones did not contain the 3' end of the putative ORF. Accordingly, 3' RACE was performed using the primers of SEQ ID NOS: 17 and 18.

```
SEQ ID NO: 17: GR-SiOMT2-FW:
5'-gaagatcgccccatgagcatgaaaccctt

SEQ ID NO: 18: SiOMT2-NEST-FW:
5'-aacgtcgttctgggagcagaaaga
```

The nucleotide sequences of the amplified fragments obtained by the RACE method were determined by the primer walking method to obtain the nucleotide sequence information including the full-length open reading frames of the SiOMT1 and SiOMT2 genes (SEQ ID NO: 1 and SEQ ID NO: 19).

SiOMT1 and SiOMT2 shared 29% amino acid sequence identity with each other. The Clustal W alignment program (Mac Vector ver. 7.2.2, Symantec Corporation) was run under the default settings for the sequence identity.

The full-length cDNA sequences of the SiOMT genes obtained were subjected to a Blastx analysis (http://www.ncbi.nlm.nih.gov/BLAST/) to determine homology to known proteins. The conditions for the Blastx analysis are as follows.

Program: Blastx ver. 2.2.9, Database: nr, Genetic code: standard (1), Filter: LOW complexity, Expect: 10, Word size: 3, Matrix: BLOSUM62, Gap Costs: Existence 11, Extension 1.

As a result of the Blastx analysis, SiOMT1 showed 74% sequence identity with Catharanthsus roseus caffeic acid-O-methyltransferase (COMT) (AAK20170), and SiOMT2 showed 57% sequence identity with Orcinol-O-methyltransferase (OOMT) of Rosa hybrida (AAM23004). As such, it cannot be said that the sequence identity of the two SiOMTs with known methyltransferase was high. Thus, the functions of the two SiOMT genes obtained could not be estimated. In other words, it is highly likely that the two SiOMT genes obtained are lignan methyltransferases not hitherto isolated.

Example 4

Construction of Escherichia coli Expression Vectors

Using a pair of primers of SEQ ID NOS: 20 and 21 for SiOMT1, a fragment carrying the BglII site upstream of the initiation methionine codon (ATG) and the SalI site downstream of the termination codon of cDNA was amplified by PCR.

Meanwhile, using a pair of primers of SEQ ID NOS: 22 and 23 for SiOMT2, a fragment carrying the BamHI site upstream of the initiation methionine codon (ATG) and the XhoI site downstream of the termination codon of cDNA was amplified by PCR. The primers used for PCR are shown below.

```
SEQ ID NO: 20: Bgl2-SiOMT1-FW:
5'-aaaacatgtatggcggatcagtccgaggaagaagaggcttt

SEQ ID NO: 21: SalI-SiOMT1-RV:
5'-attgtcgacttatgaaattccatgatccaaatatt

SEQ ID NO: 22: BamHI-SiOMT2-FW:
5'-aaaggatccatggcgatggttaaccaaaagcaaaatctt

SEQ ID NO: 23: XhoI-SiOMT2-RV:
5'-aaactcgagttaaggatatatctcgatgatagatctcaa
```

The solution (25 μl) for PCR is composed of the sesame seed cDNA as a template, 0.2 pmol/μl of each primer, 1× KOD plus buffer (TOYOBO), 0.2 mM dNTPs, 1 mM MgSO$_4$ and 1U KOD plus polymerase. Amplification was performed by PCR, after reacting at 94° C. for 5 minutes, in 30 cycles of 94° C. for 1 minute, 55° C. for 1 minute and 72° C. for 2 minutes, followed by maintaining at 72° C. for 3 minutes. Each of the PCR products obtained was inserted into the multicloning site of pCR4 Blunt-TOPO vector (Invitrogen) according to the protocol recommended by the manufacturer to give SiOMT1/pCR4 Blunt-TOPO (termed pSPB2678) and SiOMT2/pCR4 Blunt-TOPO (termed pSPB2679).

The nucleotide sequences of the SiOMT contained in pSPB2678 and pSPB2679 were analyzed to confirm that PCR was performed correctly. These plasmids were digested at the restriction enzyme site incorporated in the PCR primers. The DNA fragment of about 1.1 kb bearing the resulting full-length SiOMT was inserted into the BamHI/SalI site of Escherichia coli expression vector pQE30 (QIAGEN) to give SiOMT1/pQE30 (termed pSPB2690) and SiOMT2/pQE30 (termed pSPB2686).

Example 5

Preparation of Recombinant Proteins

Escherichia coli JM109 (TOYOBO) was transfected with the Escherichia coli expression vectors pSPB2690 and pSPB2686 constructed as described above and the transformants were incubated at 37° C. overnight in LB medium supplemented with 20 μg/ml of ampicillin in a final concentration. An aliquot of the preculture was inoculated into M9 medium (10 ml) supplemented with 50 μg/ml of ampicillin and 0.5% Casamino acid, and shake culture was continued for the time necessary to reach $A_{600}$=0.6-1.0.

Next, IPTG (Isopropyl-β-D-thiogalactopyranoside) at a final concentration of 0.5 mM was added to the culture broth. Further shake culture at 30° C. overnight was followed by centrifugation at 4° C. for 10 minutes to collect the cells. The cells were suspended in 10 ml of buffer (30 mM Tris-HCl (pH7.5), 2 mM MgCl$_2$, 0.5 mM EDTA, 50 μM APSMF), ultrasonicated to disrupt Escherichia coli and then centrifuged at 15,000 rpm at 4° C. for 10 minutes. The resulting supernatant was used as a crude enzyme solution for the following activity assay.

Example 6

Analysis of Products Obtained with Sesame Lignan Methyltransferase

Sesame lignan used as a substrate for the enzyme reaction was dissolved in a small quantity of DMSO and then in 70% ethanol to prepare the substrate solution (1 mg/ml). Sesame lignan can be produced, for example, by extracting and purifying from sesame in accordance with publicly known methods (J. Bioscience, Biotechnology and Biochemistry, 67: 1693 (1993)). After 10 μl of the substrate solution, 200 μl of the aforesaid crude enzyme solution of SiOMT expressed in *Escherichia coli* and 10 μl of 10 mM S-adenosyl-L-methionine (SAM) were mixed in a reaction tube, the mixture was reacted at 30° C. for 2 hours.

The enzyme reaction was terminated by adding 100% acetonitrile (250 μl) containing 0.1% trifluoroacetic acid (TFA) to the reaction tube. The reaction tube was vigorously agitated with a vortex mixer, followed by centrifugation at 15,000 rpm at 4° C. for 5 minutes. The resulting supernatant was washed through a filter (pore size of 0.45 mm, 4 mm Millex-LH, Millipore) and then analyzed using high performance liquid chromatography (hereinafter HPLC). The conditions for the analysis of lignans and methylated lignans are as follows.

Liquid chromatography (Lc-2010c, Shimadzu Corporation) was performed using a C-30 column (Nomura Chemical, C30-UG-5, 4.6 mM×150 mM). In the mobile phase, 0.1% TFA and 0.1% TFA-containing 90% acetonitrile were used as eluent A and eluent B, respectively. The column was equilibrated with a mixture of 80% eluent A and 20% eluent B (20 minutes), and eluted with a linear gradient (80% eluent A:20% eluent B→10% eluent A:90% eluent B) for 20 minutes (flow rate of 0.6 ml/min.) and then with 10% eluent A: 90% eluent B for 7 minutes. Absorption was monitored at 280 nm to detect the compounds contained in a sample. The spectra between 190 nm and 400 nm for each peak of the compounds were measured using SPD-10AV (Shimadzu Corporation) to detect substances having two absorption maxima (230 nm and 280 nm) characteristic of lignans. Under the conditions, authentic pinoresinol is detected at about 11.8 minutes, authentic piperitol at about 15.5 minutes and authentic sesaminol at about 16.8 minutes.

Figure 3:
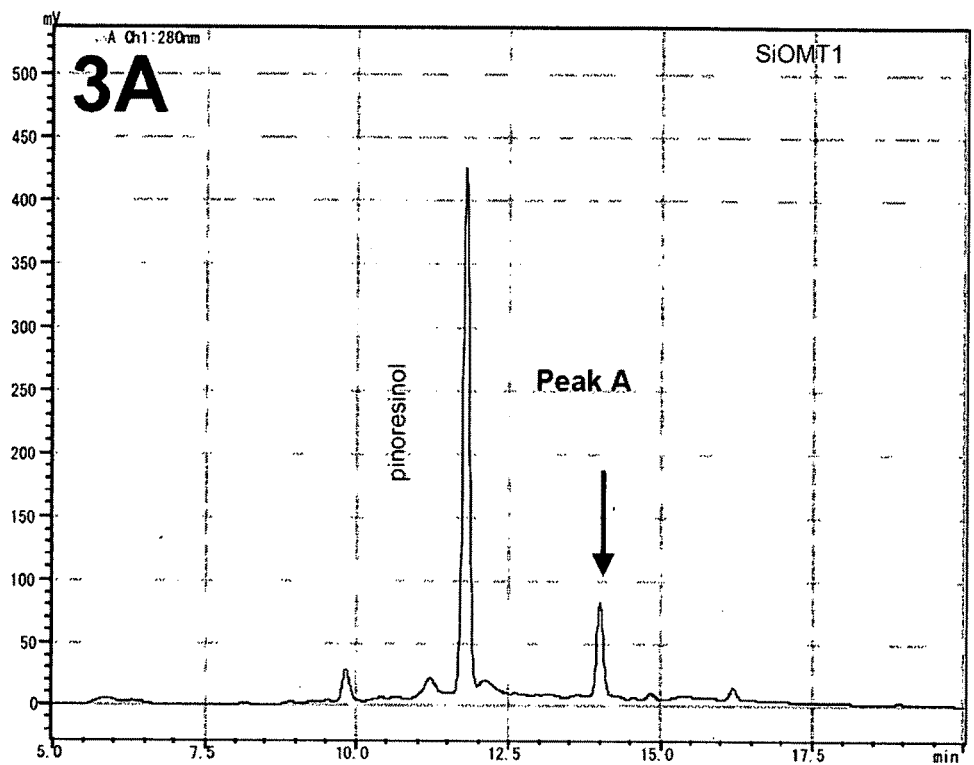
Figure 3:
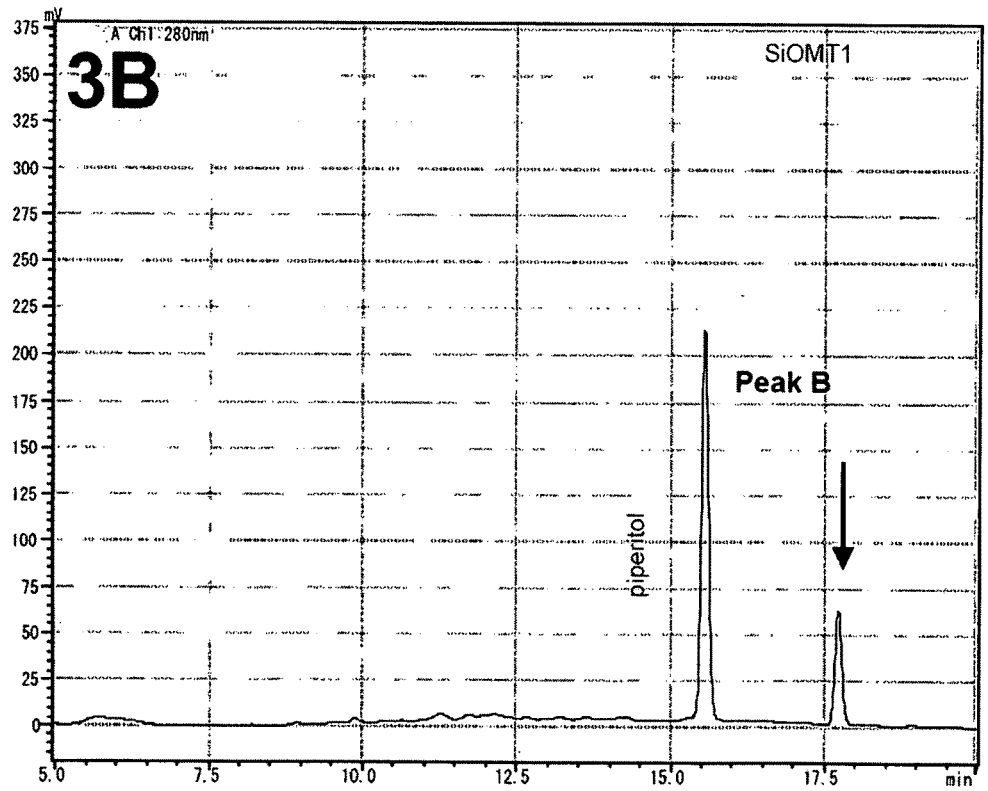

In the reaction solution of the SiOMT1 recombinant protein and pinoresinol, peak A having the spectrum of lignan with a retention time of about 14.0 minutes was newly obtained (FIG. 3-3A). Further in the reaction solution of the SiOMT1 recombinant protein and piperitol, peak B having the spectrum of lignan with a retention time of about 17.7 minutes was newly obtained (FIG. 3-3B).

Figure 4:
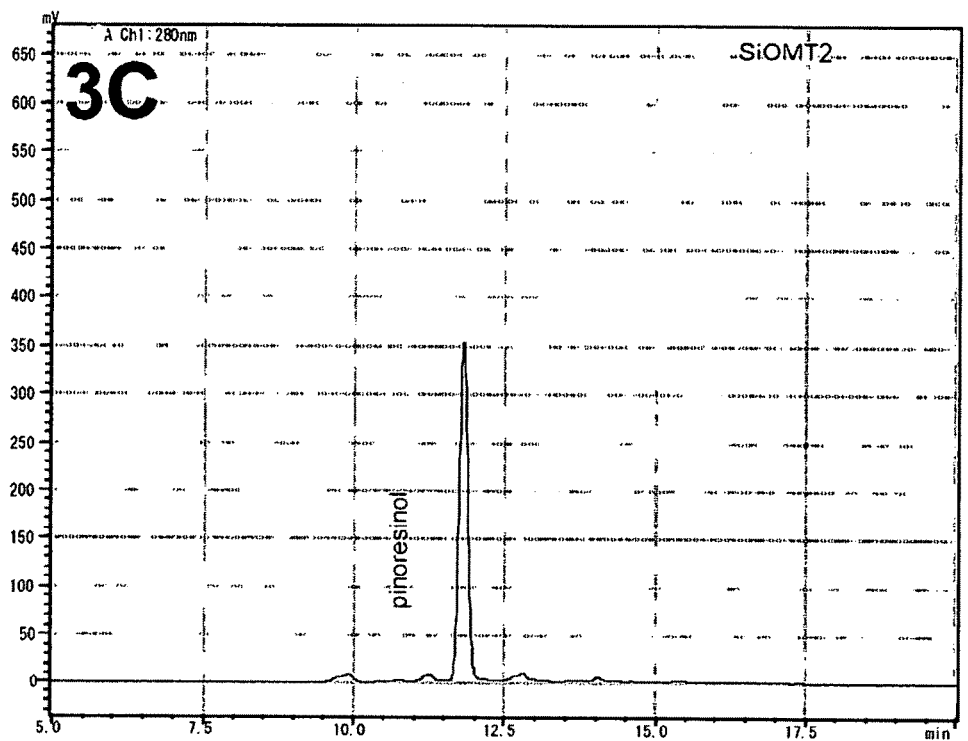
Figure 4:
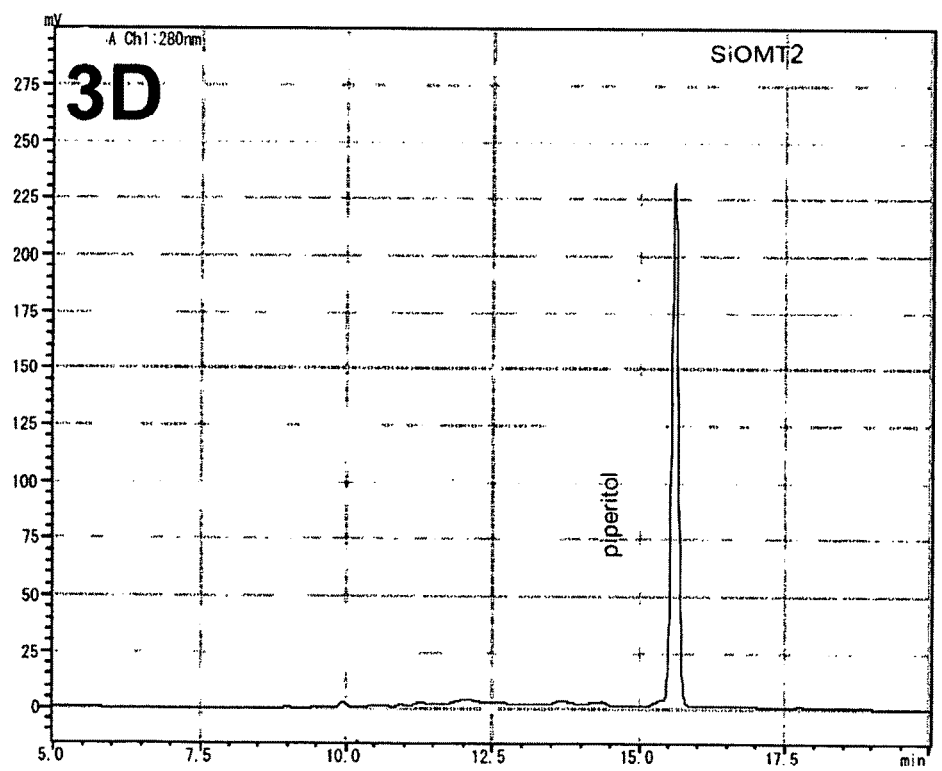

In the reaction solution of the SiOMT2 recombinant protein and pinoresinol or piperitol, any new product was not detected (FIGS. 4-3C-3D). The lignan methylation activity of SiOMT1 and SiOMT2 on sesaminol was not observed.

Next, the molecular weight of the novel lignan produced with SiOMT1 was determined by the LC-MS analysis (liquid chromatography (LC): Waters 2795 (Waters Inc.), mass spectrograph: QUATRO micro (MICROMASS, Inc.)). A column packed with 1 ml of Diaion HP-20 resin (Mitsubishi Chemical) was washed with 5 ml of 50% acetone and then equilibrated with 10 ml of water. The enzyme reaction solution containing the methylated lignan produced with SiOMT1 was loaded on the column and impurities were washed off with 5 ml of water. Elution was then performed with 2 ml of 80% acetone. After the eluant was evaporated to dryness using an evaporator, the residue was dissolved in 90% acetonitrile (100 μl) containing 1% formic acid and the solution was provided as a sample for the LC-MS analysis. The conditions for LC are shown below.

Using a Develosil C30-UG-3 column (Nomura Chemical, 3.0×150 mm), water as eluent A, 100% acetonitrile as eluent B, 1% formic acid as eluent C and 100 mM ammonium acetate aqueous solution as eluent D were used for the mobile phase. Elution was performed with a linear gradient (60% eluent A:30% eluent B:5% eluent C:5% eluent D→10% eluent A:80% eluent B:5% eluent C:5% eluent D) for 10 minutes (flow rate: constantly 0.2 ml/min.) and then with 10% eluent A:80% eluent B:5% eluent C:5% eluent D for 5 minutes (flow rate: always 0.2 ml/min.). Signals were detected as ammonium adduct ions.

Figure 5:
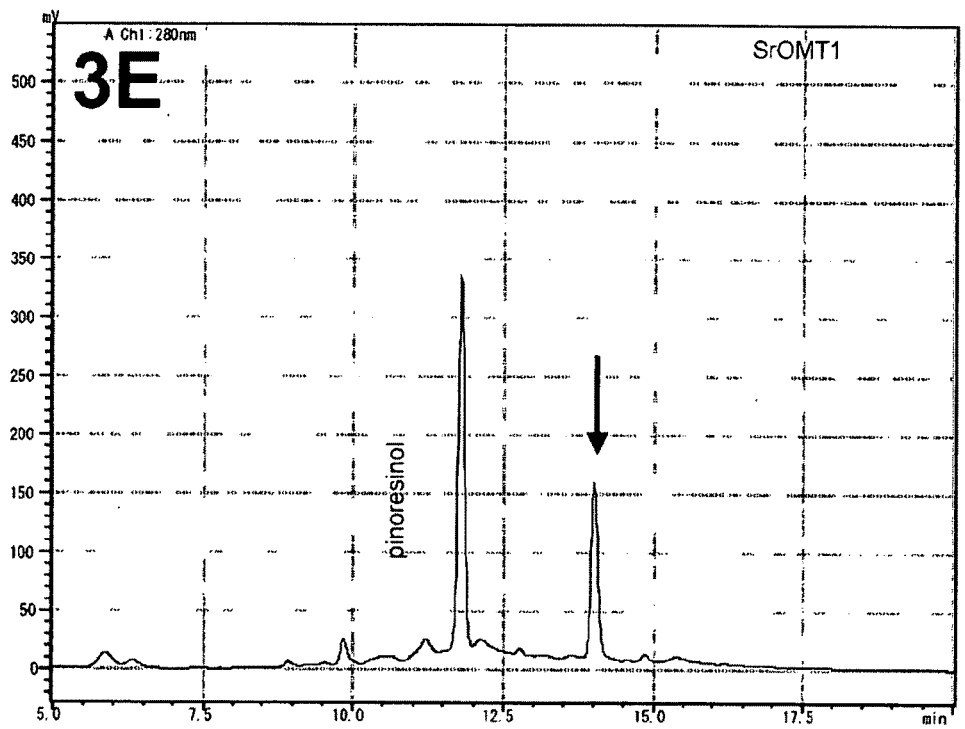
Figure 5:
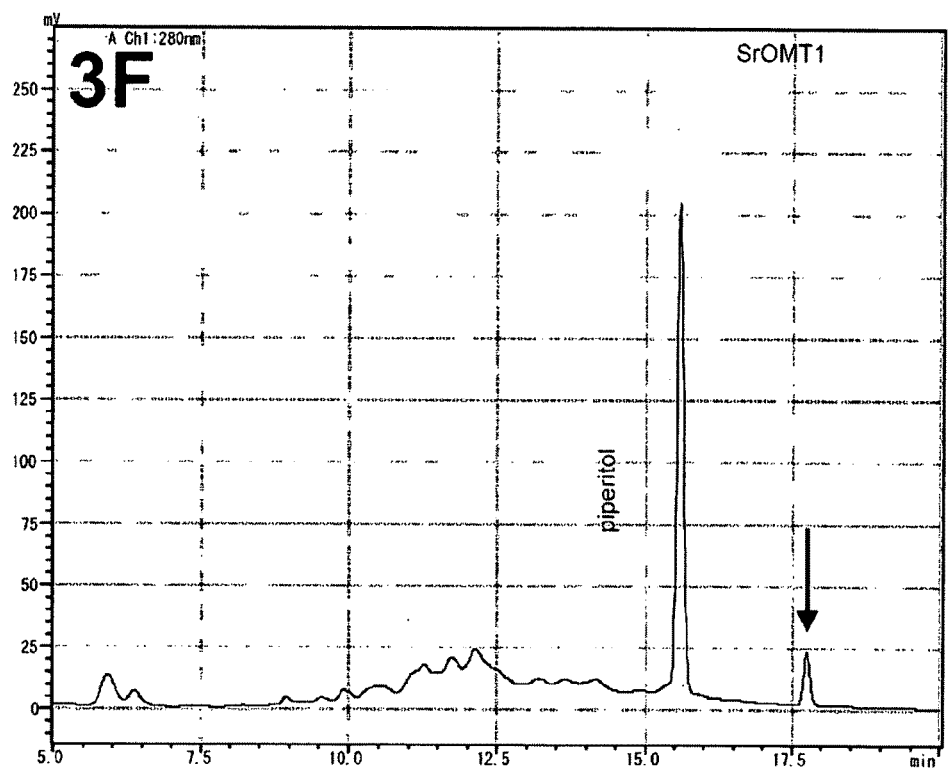
Figure 6:
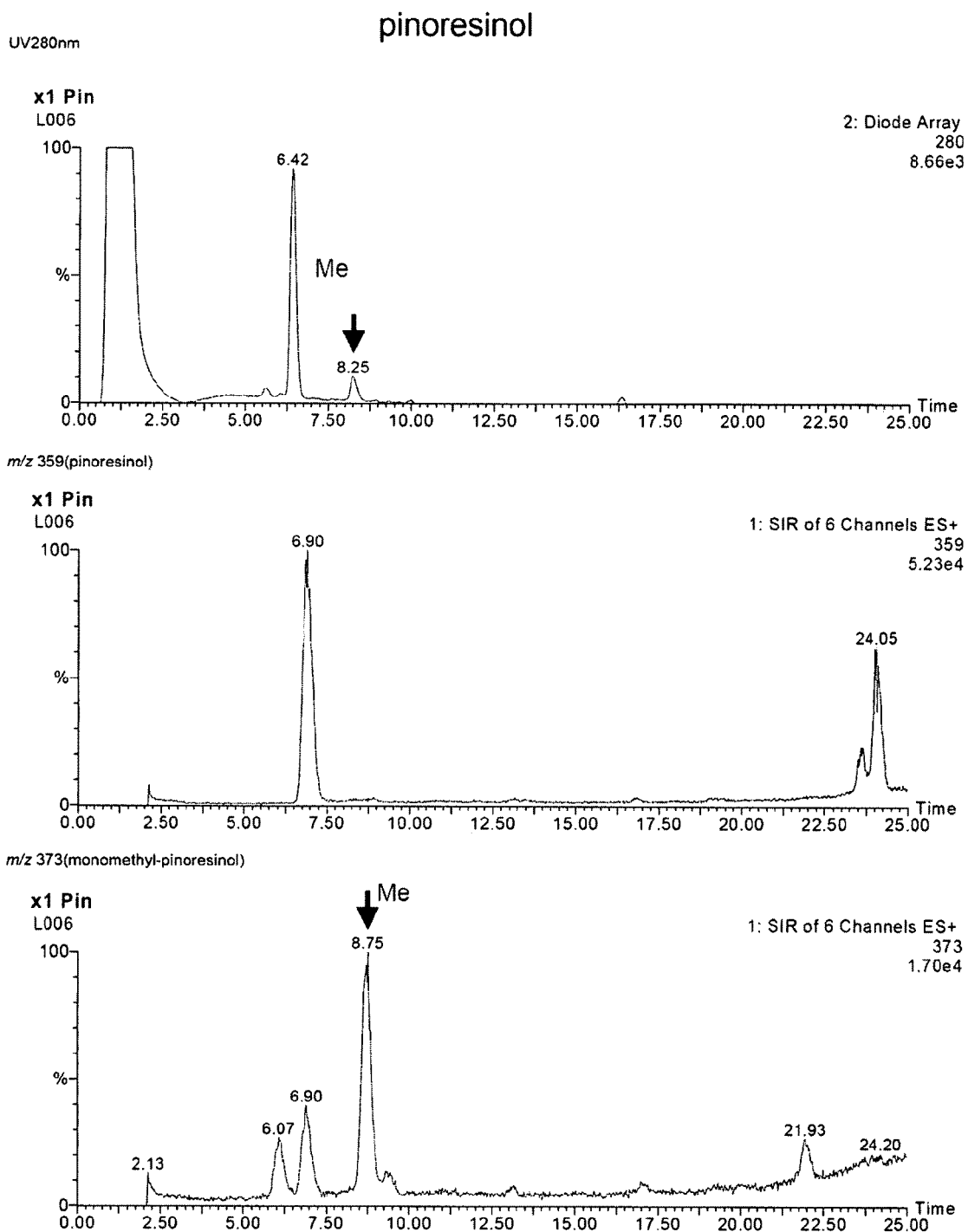
Figure 7:
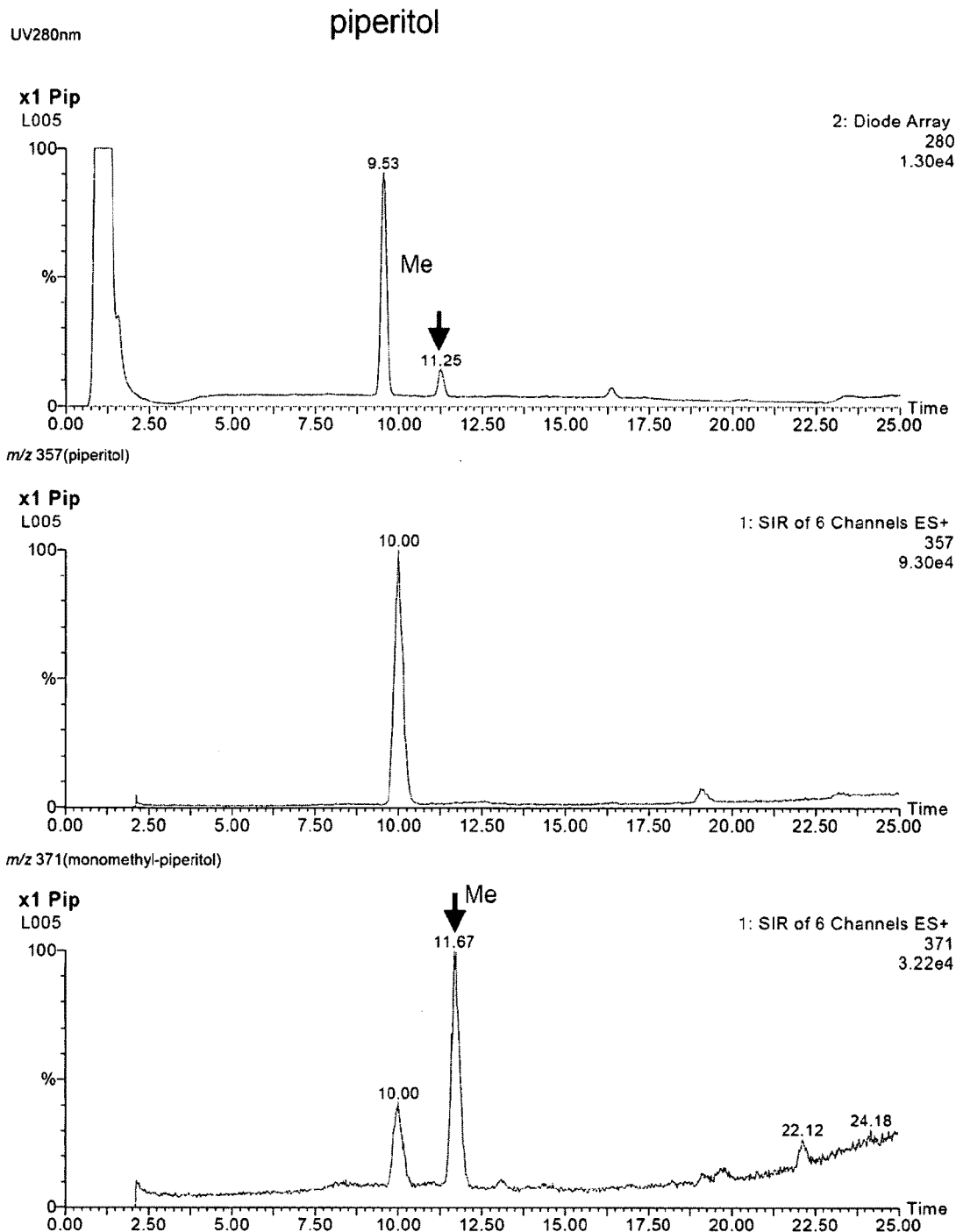

Under the conditions, peak A is detected at about 8.3 minutes and peak B at about 11.3 minutes (FIGS. 3-5). The MS conditions of ion mode: ES+, cone voltage: 15V and collision 2 eV were used for MS scanning in the range of 210 to 400 (m/z, 30 mins.) to measure PDA in the range of 210 to 400 nm (30 minutes).

As a result of the LC-MS analysis under the foregoing conditions, peak A had the molecular weight of ammonium ion adduct at 373 (m/z) and peak B had the molecular weight of ammonium ion adduct at 371 (m/z) (FIG. 6-4A and FIG. 7-4B). Accordingly, these peaks were identified to be monomethylated pinoresinol (molecular weight of ammonium ion adduct, 359) and monomethylated piperitol (molecular weight of ammonium ion adduct, 374), respectively.

The foregoing results reveal that SiOMT1 is an enzyme having the monomethylation activity on the sesame lignans, pinoresinol and piperitol.

Example 7

Isolation of Sesame Lignan Methyltransferase Homolog Gene

In order to clarify that functions of the enzyme gene having the lignan methylation activity are functionally and structurally conserved in sesame species, it was attempted to isolate the counterpart gene (SrOMT1) of SiOMT1 from African sesame Sesamum radiatum cytogenetically different from Sesamum indicum as a domesticated cultivar of sesame.

*S. radiatum*, a sesame plant actually grown in Africa and India, is considered to have the chromosome number of 2n=64 by cytogenetic analysis, and phylogenetically different from *S. indicum* (2n=26) of domesticated cultivar of sesame (Reference Literature: Mitsuo Namiki, Teisaku Kobayashi, "Goma-no-Kagaku" (Science of Sesame), Asakura Publishing Co.). However, it is known that a wide variety of lignans are accumulated also in the seed of *S. radiatum* (Reference Literature: Bedigian, D. et al., Biochemical Systematics and Ecology 13: 133-139 (1985)). It is therefore expected that a gene corresponding to SiOMT1 of *S. indicum* would be contained in the genome of *S. radiatum*.

It was attempted to amplify SrOMT1 by PCR using cDNA from the *S. radiatum* seed and a pair of primers Bgl2-SiOMT1-FW (SEQ ID NO: 20) and SalI-SiOMT1-RV (SEQ ID NO: 21).

The solution is composed of 1 μl of cDNA from the *S. radiatum* seed, 1× Ex-Taq buffer (TaKaRa), 0.2 mM dNTPs, 0.2 pmol/μl of each primer and 1.25 U Ex-Taq polymerase. PCR was carried out, after reacting at 94° C. for 5 minutes, in 30 cycles of 94° C. for 1 minute, 55° C. for 1 minute and 72° C. for 2 minutes, followed by maintaining at 72° C. for 5 minutes. The resulting PCR product of about 1.1 kb was inserted into the multicloning site of pCR2-TOPO vector (Invitrogen) according to the protocol recommended by the manufacturer to obtain SrSiOMT1/pCR2-TOPO (pSPB2910).

The nucleotide sequence (and amino acid sequence) of SrOMT1 contained in pSPB2910 was determined by the primer walking method (SEQ ID NOS: 3 and 4). SrOMT1 showed 89% amino acid sequence identity with SiOMT1. For the sequence identity, the Clustal W alignment program (Mac Vector ver. 7.2.2, Symantec Corporation) was run under the default settings. This high sequence identity strongly supports that SrOMT1 is the counterpart gene of SiOMT1.

RT-PCR was performed in a manner similar to EXAMPLE 2 and expression of the gene specific to the seed of SrOMT1 was confirmed (FIG. 2-2B).

*Escherichia coli* expression vector SrOMT1/pQE30 (pSPB2911) for SrOMT1 was constructed as in EXAMPLE 4, the recombinant protein was prepared as in EXAMPLE 5, and the activity and product were analyzed as in EXAMPLE 6.

SrOMT1 exhibited the methylation activity on pinoresinol and piperitol as SiOMT1 did (FIG. 5). SiOMT1 did not show any methylation activity on sesaminol. These results reveal that SrOMT1 is the counterpart gene of SiOMT1, indicating that this enzyme gene is conserved in sesame species.

Example 8

Genomic Southern Analysis of SiOMT1

Genomic Southern analysis was performed to elucidate the copy number of SiOMT1 gene in sesame genome. Genomic DNA was extracted from the leaves of *S. indicum* (Masekin cultivar) using Nucleon Phytopure for Plant Extraction Kit (Amersham) according to the protocol recommended by the manufacturer. After 20 μg of the genomic DNA extracted was digested with EcoRI, HindIII, XhoI or XbaI, the digestion products were separated by electrophoresis using agarose gel. This agarose gel was hydrolyzed in 0.25M HCl for 15 minutes, then denatured with a solution of 1.5M NaCl/0.5M NaOH (30 minutes) and neutralized in a denaturing solution (20 minutes) by adding 1.5 M NaCl-containing Tris-HCl (pH 7.5). Next, the genomic DNA in the agarose gel was transferred to membrane (Hybribond-N, Amersham) in 20×SSC solution. The membrane-transferred genomic DNA was bound to the membrane by UV exposure and prehybridized at 42° C. for an hour using a hybridization buffer (High SDS buffer: Roche) composed of 7% SDS, 50% formamide, 5×SSC, 2% blocking reagent, 0.1% lauroylsarcosine and 50 mM sodium phosphate buffer (pH 7.0).

Using pSPB2678 as a template, PCR was performed using a pair of primers of SEQ ID NO: 20 (Bgl2-SiOMT1-FW) and SEQ ID NO: 21 (SalI-SiOMT1-RV) to prepare DIG-labeled hybridization probes. The solution for PCR is composed of 1 ng of the pSPB2678 plasmid, 1×PCR buffer (Takara Bio Inc.), 2.5 mM DIG-dNTP mixture (PCR DIG labeling Mix, Roche), 0.2 pmol of each primer and 1U rTaq polymerase (Takara Bio Inc.). PCR was carried out by repeating 30 cycles of 95° C. for 30 seconds, 53° C. for 30 seconds and 72° C. for 2 minutes. The PCR product purified on Sephadex G-50 column-Fine (Boehringer) was used as the hybridization probe. After this probe was heat denatured, 15 μl of the probe was added to the prehybridization solution, followed by incubation at 42° C. overnight.

After hybridization, the membrane was washed under high stringent conditions (twice with a solution containing 0.2× SSC and 0.1% SDS at 65° C. for 30 minutes). Hybridization signals were detected using DIG Labeling & Detection Kit (Roche) according to the protocol recommended by the manufacturer.

Figure 8:
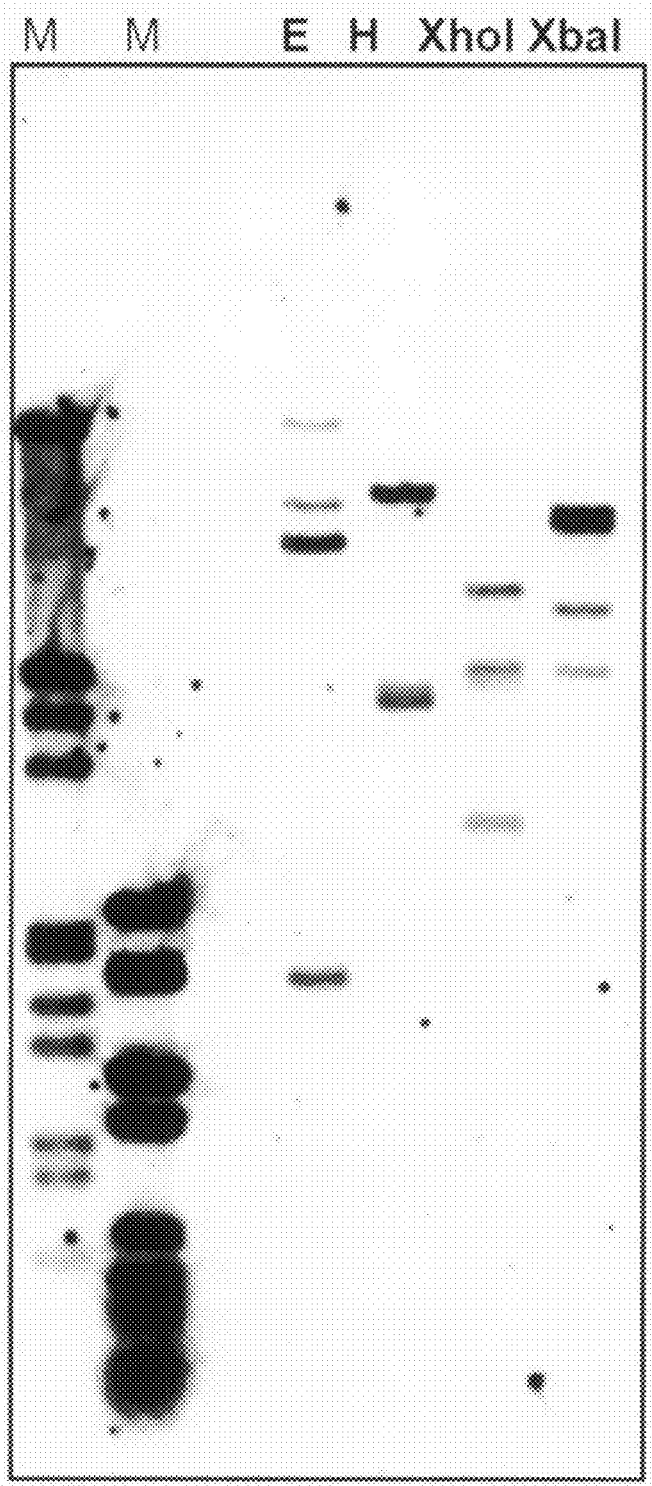
FIG. 8 is the results of genomic Southern hybridization using a full-length probe for the SiOMT1 gene.

As a result of the Southern analysis, two or more bands were detected also in all of the restriction enzyme digestion fragments, indicating that at least one gene having an extremely high homology to SiOMT1 was encoded in the sesame genome (FIG. 8). It is also expected that a plurality of enzyme genes which functionally overlap with or resemble to SiOMT1 would be present in the sesame genome.

Example 9

Assay for COMT Activity of Sesame Lignan Methyltransferase

As shown in EXAMPLE 3, SiOMT1 and SrOMT1 shared the highest sequence identity with COMT in the known proteins according to the database search. This suggests that sesame methyltransferase also has the COMT activity.

The methyltransferase activity of SiOMT1 and SrOMT1 expressed in EXAMPLES 5 and 7 on caffeic acid was studied. In a reaction tube, 10 μl of 0.4 mg/ml caffeic acid, 200 μl of the crude enzyme solution of SiOMT expressed in *Escherichia coli* and 10 μl of 10 mM SAM were mixed, and the mixture was reacted at 30° C. for an hour. The product was then provided for HPLC analysis in a manner similar to EXAMPLE 6.

Figure 9:
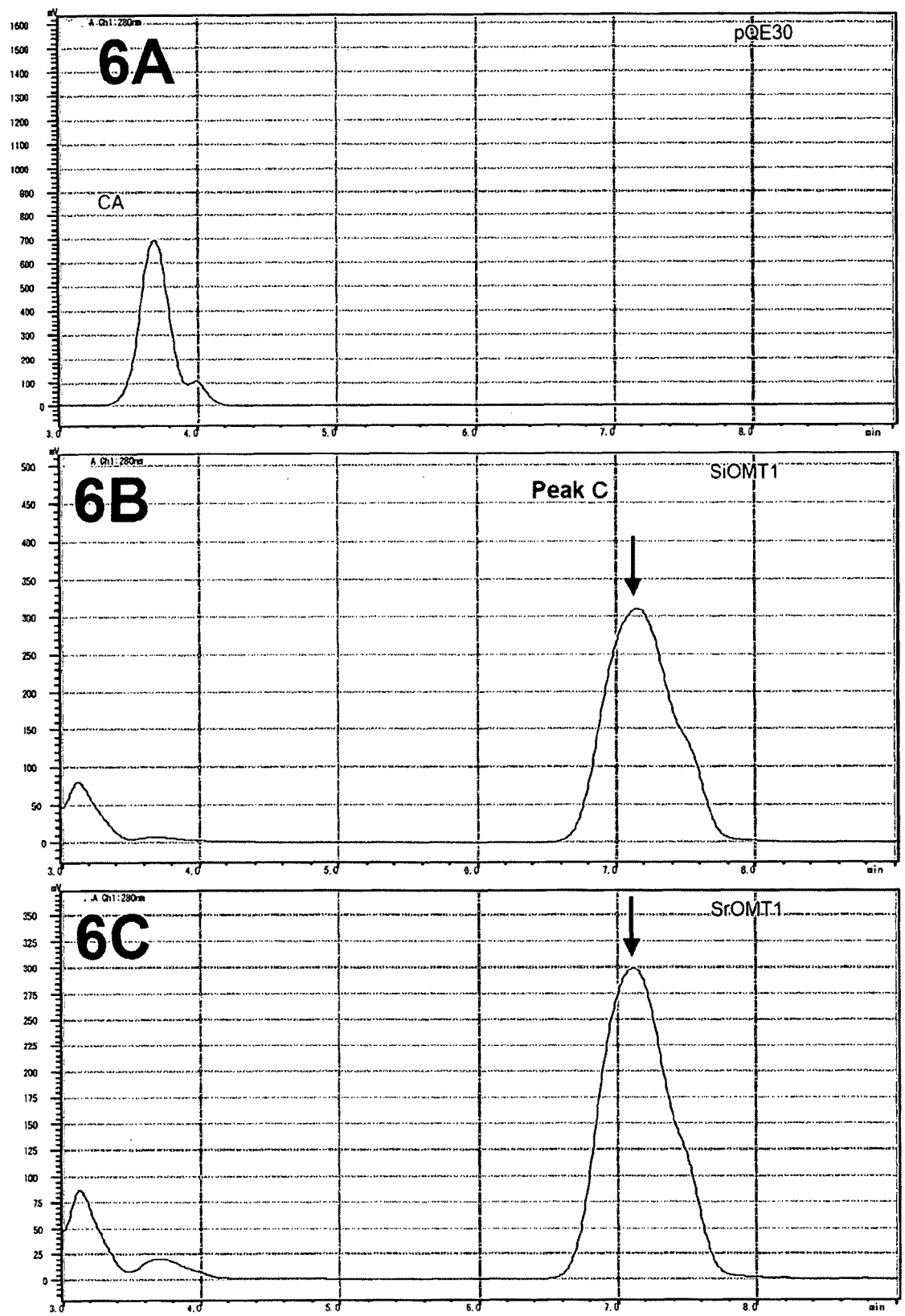

As a result, peak C (retention time of about 7.3 minutes), which was the same as ferulic acid as the reference standard in retention time, appeared in the reaction solution with caffeic acid for both SiOMT1 and SrOMT1 (FIGS. 9-6A to 6C). Caffeic acid was eluted at retention time of about 3.9 minutes under the conditions for this HPLC analysis.

Figure 10:
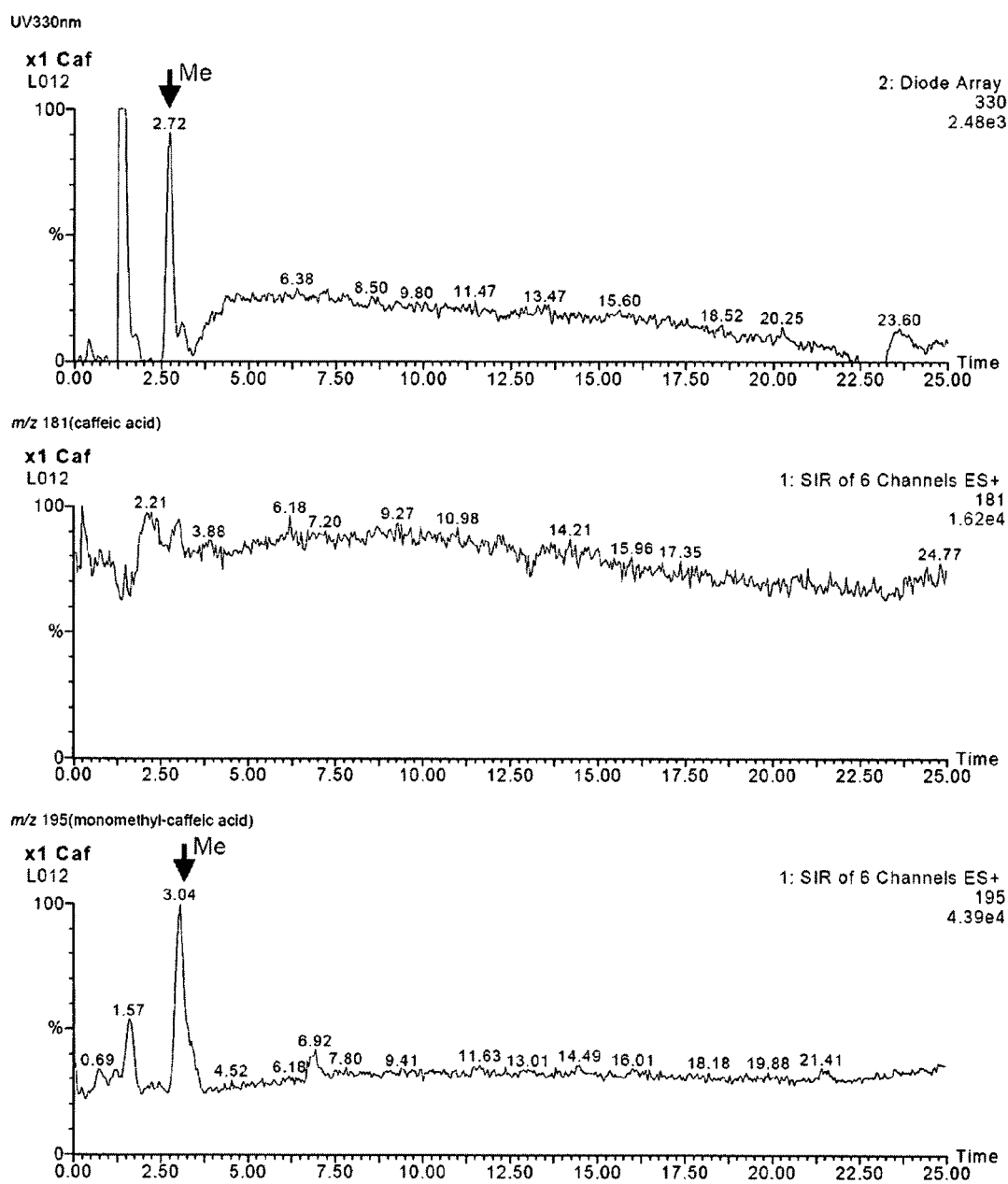

When LC-MS analysis was performed under the same conditions as in EXAMPLE 6, peak C had the molecular weight of ammonium ion adduct at 195 (m/z) (FIG. 10-6D). It was thus confirmed that peak C was ferulic acid produced by monomethylation of caffeic acid (molecular weight of ammonium ion adduct at 181 (m/z)). These results revealed that the two lignan methyltransferases also had the COMT activity.

INDUSTRIAL APPLICABILITY

As described above, the polypeptide and polynucleotide of the present invention are useful for producing the methylated lignans. In addition, the transformants or cells, in which the polynucleotide of the present invention is introduced to be capable of expressing the same, are extremely useful for producing the methylated lignans or products using the same, in the food sector and a variety of other industry sectors. Where the transformant above is a plant, the plant itself can be used as foodstuff and is thus very useful in the agriculture sector, etc.

Moreover, by using the polypeptide and polynucleotide of the present invention in combination with the other enzymes (piperitol and sesamin synthase SiP189) discovered by the present inventors, the production system of not only sesame but also particular lignan molecule species can be established so that the production volumes of particular lignan and methylated lignans can be expanded. Accordingly, the present invention is widely used in agriculture, food industry and drug industry as well as industries related thereto.

The invention claimed is:

1. An isolated polynucleotide as defined in any one of (a) through (d) below:
   (a) an isolated polynucleotide comprising a polynucleotide consisting of the nucleotide sequence of SEQ ID NO: 1;
   (b) an isolated polynucleotide comprising a polynucleotide encoding a protein consisting of the amino acid sequence of SEQ ID NO: 2;
   (c) an isolated polynucleotide consisting of a nucleotide sequence having at least 95% identity to SEQ ID NO:1, wherein the polynucleotide encodes a protein having the activity of transferring a methyl group to a lignan; and,
   (d) an isolated polynucleotide comprising a polynucleotide encoding a protein consisting of the amino acid sequence that has been modified by substitution, deletion, insertion, and/or addition of one to six amino acids of SEQ ID NO: 2 and having an activity of transferring a methyl group to a lignan.

2. The polynucleotide according to claim 1, which comprises a polynucleotide consisting of the nucleotide sequence of SEQ ID NO: 1.

3. The polynucleotide according to claim 1, which comprises a polynucleotide encoding a protein consisting of the amino acid sequence of SEQ ID NO: 2.

4. The polynucleotide according to claim 1, which is a DNA.

5. The polynucleotide according to claim 1, which encodes a protein having an activity of transferring a methyl group to a furofuran lignan.

6. The polynucleotide according to claim 5, which encodes a protein having an activity of transferring a methyl group to pinoresinol and/or piperitol.

7. An isolated protein encoded by the polynucleotide according to claim 1.

8. A vector comprising the polynucleotide according to claim 1.

9. A host cell transformed by the vector according to claim 8.

10. A method of producing a protein having an activity of transferring a methyl group to a lignan, which comprises culturing or growing the host cell according to claim 9 and collecting said protein from said host cell.

11. A plant transformed with the polynucleotide according to claim 1, or a plant which is a progeny of said plant having the same properties as the plant, or a tissue of these plants.

12. A method of transferring a methyl group to a lignan, which comprises using the polynucleotide according to claim 1.

13. A plant with an altered lignan composition produced by transformation and expression of said plant with the polynucleotide according to claim 1, or a plant which is a progeny of the plant having the same properties as the plant.

* * * * *